United States Patent
Bae et al.

(10) Patent No.: US 11,279,744 B2
(45) Date of Patent: Mar. 22, 2022

(54) NEUROPEPTIDE Y FRAGMENT CAPABLE OF RELEASING HEMATOPOIETIC STEM CELLS INTO BLOOD AND TREATING OSTEOPOROSIS

(71) Applicant: Kyungpook National University Industry-Academic Cooperation Foundation, Daegu (KR)

(72) Inventors: Jae Sung Bae, Daegu (KR); Hee Kyung Jin, Daegu (KR); Min Hee Park, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 0 days.

(21) Appl. No.: 16/733,347

(22) Filed: Jan. 3, 2020

(65) Prior Publication Data

US 2020/0172592 A1 Jun. 4, 2020

Related U.S. Application Data

(63) Continuation of application No. PCT/KR2018/007504, filed on Jul. 3, 2018.

(30) Foreign Application Priority Data

Jul. 5, 2017 (KR) .................... 10-2017-0085663

(51) Int. Cl.
| | | |
|---|---|---|
| *C07K 14/575* | (2006.01) | |
| *A23L 33/18* | (2016.01) | |
| *A61P 19/10* | (2006.01) | |
| *A61K 38/00* | (2006.01) | |

(52) U.S. Cl.
CPC ........ *C07K 14/57545* (2013.01); *A23L 33/18* (2016.08); *A61P 19/10* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 2016/0060320 A1* | 3/2016 | Woldbye | ............ A61K 38/2271 514/18.1 |
| 2016/0243198 A1 | 8/2016 | Bae et al. | |
| 2017/0081366 A1 | 3/2017 | Bae et al. | |
| 2017/0189491 A1 | 7/2017 | Bae et al. | |

FOREIGN PATENT DOCUMENTS

| | | | |
|---|---|---|---|
| KR | 10-1486061 B1 | 1/2015 | |
| KR | 10-1486074 B1 | 1/2015 | |
| KR | 10-1492053 B1 | 2/2015 | |
| KR | 10-1503020 B1 | 3/2015 | |
| WO | WO 2013/078511 | * 6/2013 | ............. C07K 16/18 |

OTHER PUBLICATIONS

Rose et al., The Journal of Neuroscience, Jan. 28, 2009; 29(4):1115-1125 (Year: 2009).*
EPO and Google translation of WO02081686; downloaded May 19, 2021 (Year: 2021).*
English Translation of International Search Report corresponding to International Patent Application No. PCT/KR2018/007504 dated Nov. 15, 2018.
Park et al., "Neuropeptide Y-based Recombinant Peptides Ameliorate Bone Loss in Mice by Regulating Hematopoietic Stem/progenitor Cell Mobilization," BMB Reports, vol. 50, No. 3, pp. 138-143 (2017).
Park et al., "Role of Neuropeptide Y in the Bone Marrow Hematopoietic Stem Cell Microenvironment," BMB Reports, vol. 48, No. 12, pp. 645-646 (2015).
Liu et al., "Neuropeptide Y Stimulates Osteoblastic Differentiation and VEGF Expression of Bone Marrow Mesenchymal Stem Cells Related to Canonical Wnt Signaling Activating in Vitro," Neuropeptides, vol. 56, pp. 105-113 (2016).
English Translation of Written Opinion of the International Search Authority corresponding to International Patent Application No. PCT/KR2018/007504 dated Nov. 15, 2018.
English Translation of the International Preliminary Report on Patentability Chapter 1 corresponding to International Patent Application No. PCT/KR2018/007504 dated Jan. 7, 2020.
Supplementary European Search Report corresponding to European Patent application No. 18828211 dated May 13, 2020.

* cited by examiner

*Primary Examiner* — Christina M Borgeest
(74) *Attorney, Agent, or Firm* — Jenkins, Wilson, Taylor & Hunt, P.A.

(57) ABSTRACT

The present invention relates to a novel peptide exhibiting an effect of releasing myelopoiesis stem cells into blood and an osteoporosis therapeutic effect and use thereof and, in particularly, to a novel peptide consisting of an amino acid sequence of SEQ. ID.NO:1 which has effects of releasing hematopoietic stem cells into a bloodstream and decreasing osteoclast cells in bone narrow, and a pharmaceutical composition comprising the novel peptide as an active ingredient for preventing or treating neutropenia, anemia or osteoporosis. Because of side effects, the peptide of the present invention not only increases level of leukocytes, red blood cells and platelets in blood, but also alleviates a decrease in bone density, and therefore, can be very usefully used for the development of a prophylactic or therapeutic agent for neutropenia, anemia or osteoporosis.

7 Claims, 40 Drawing Sheets
(32 of 40 Drawing Sheet(s) Filed in Color)
Specification includes a Sequence Listing.

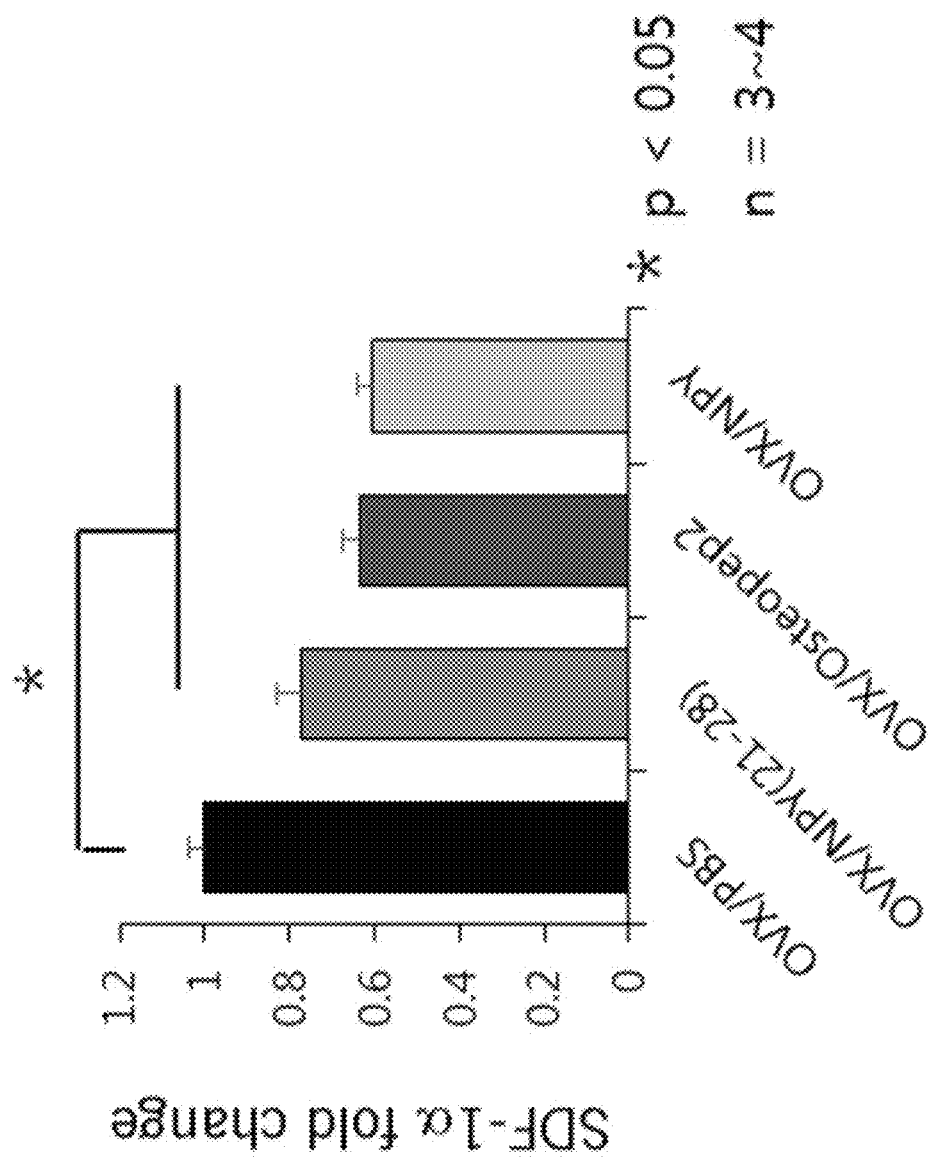

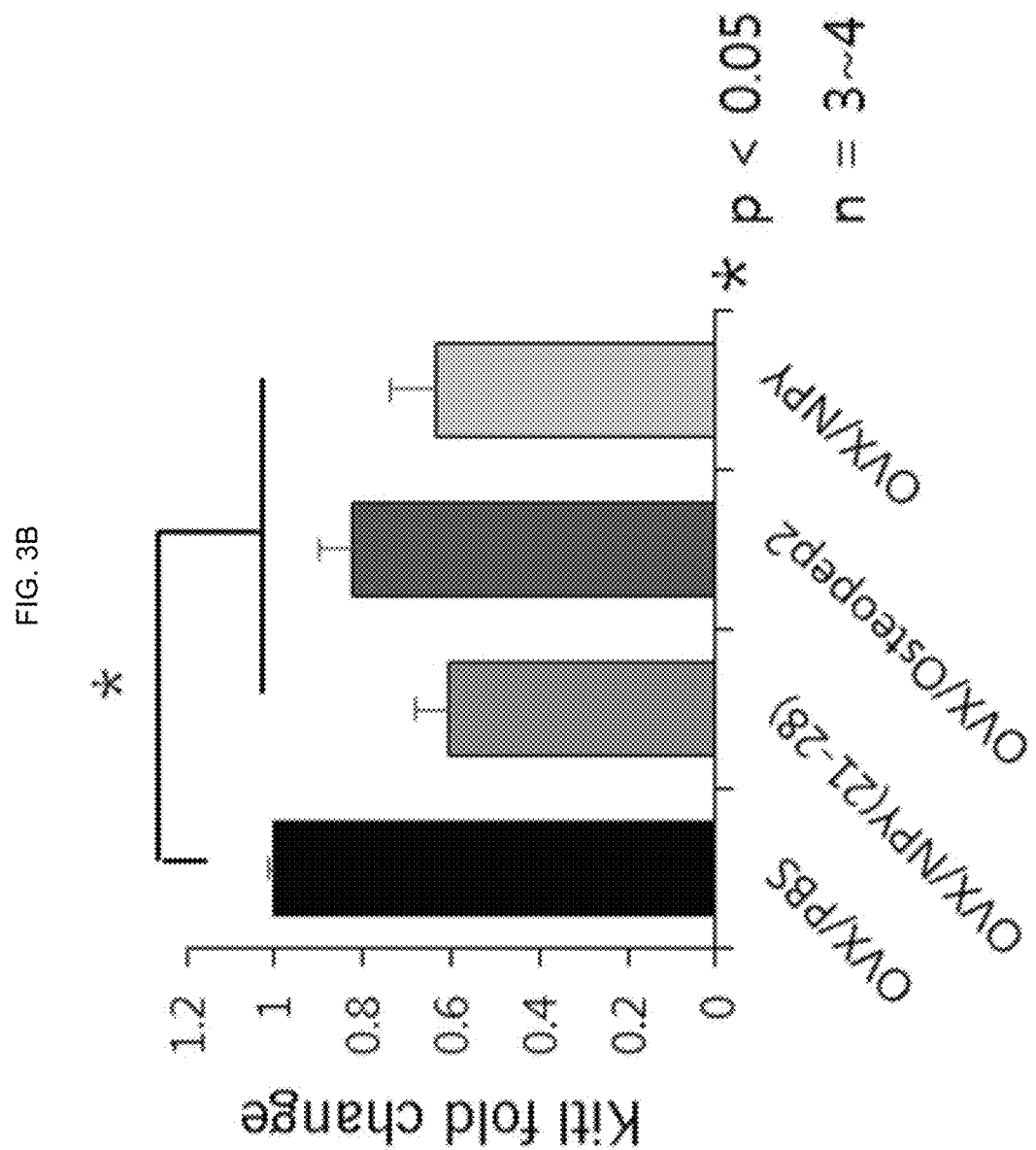

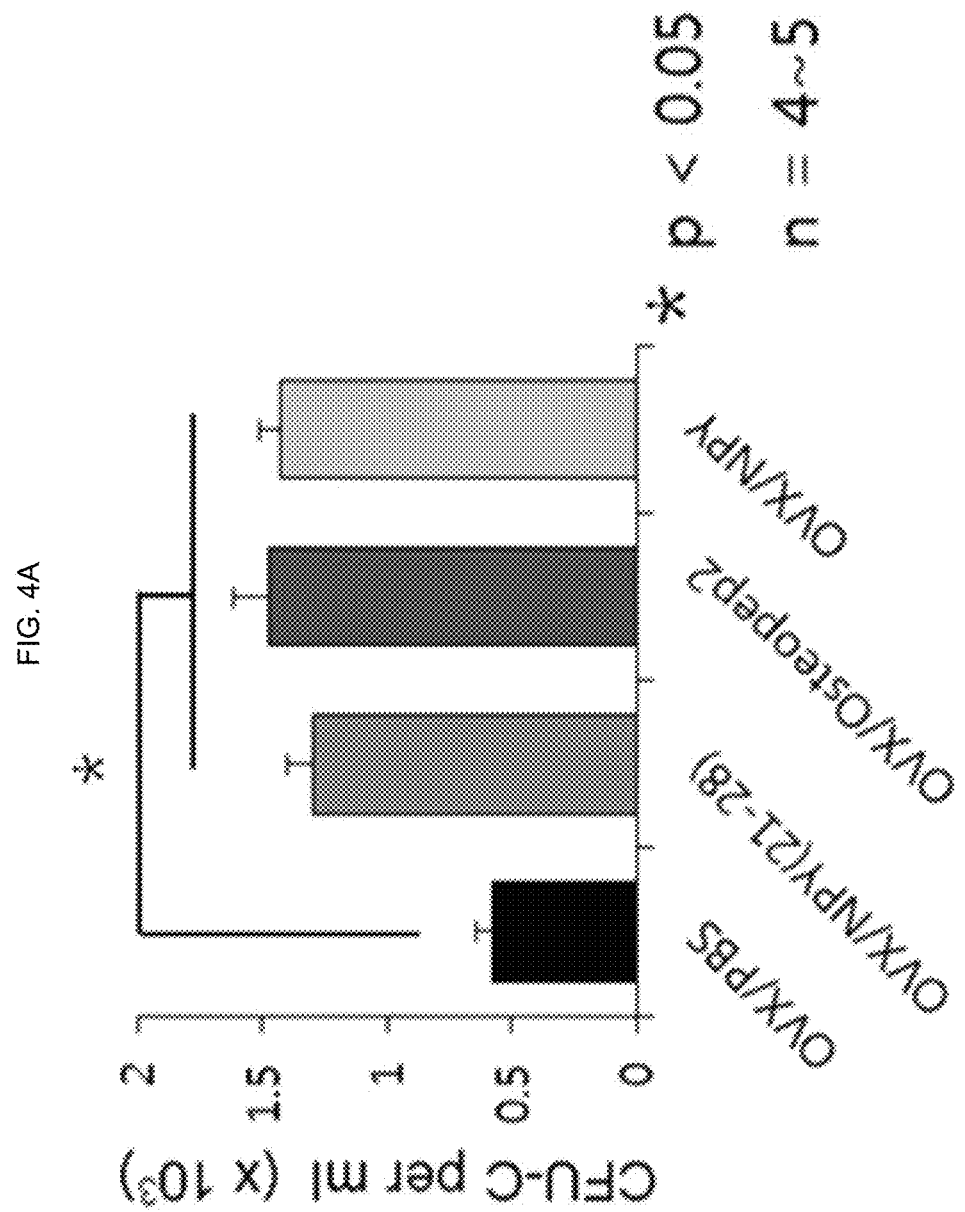

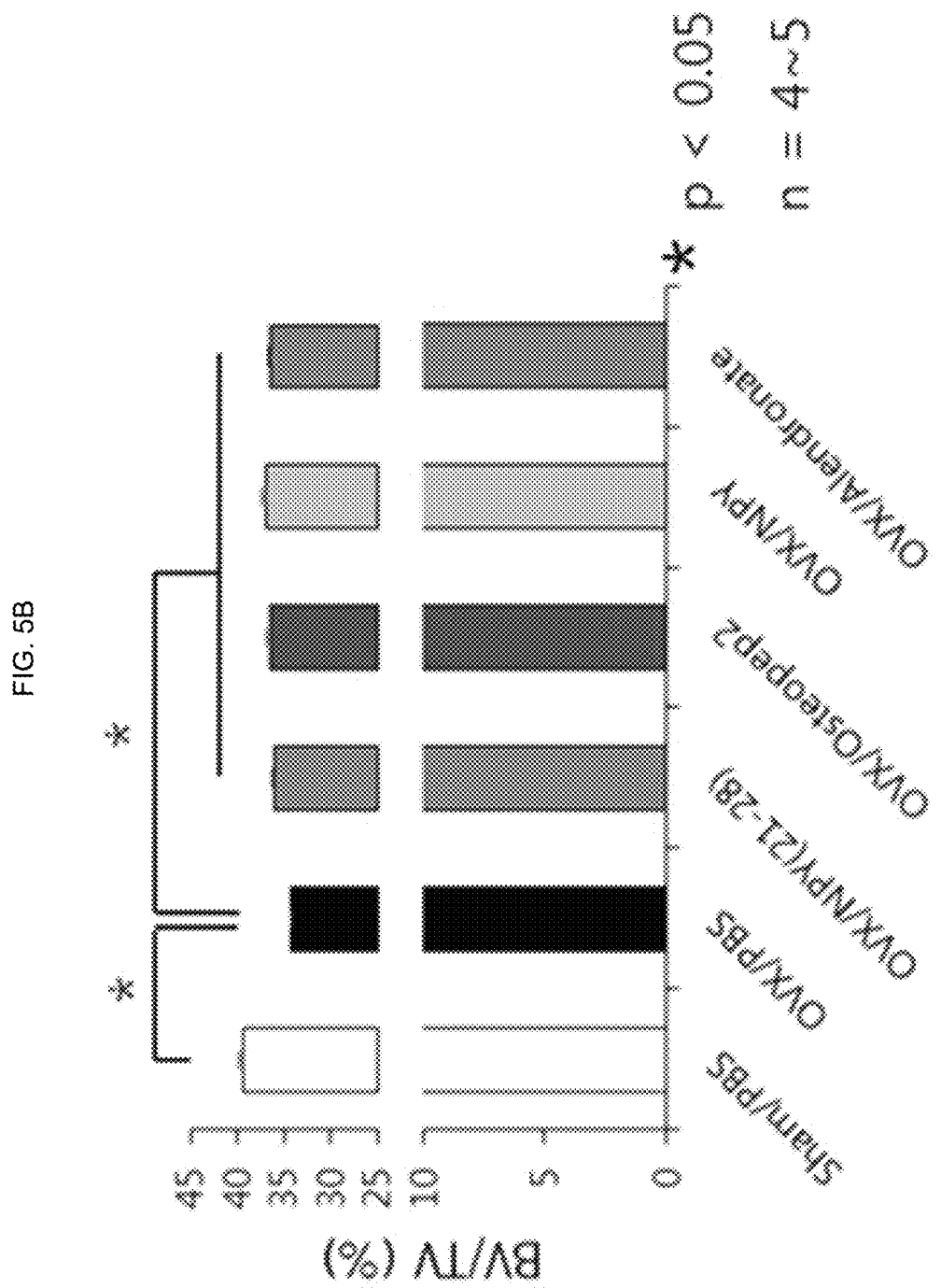

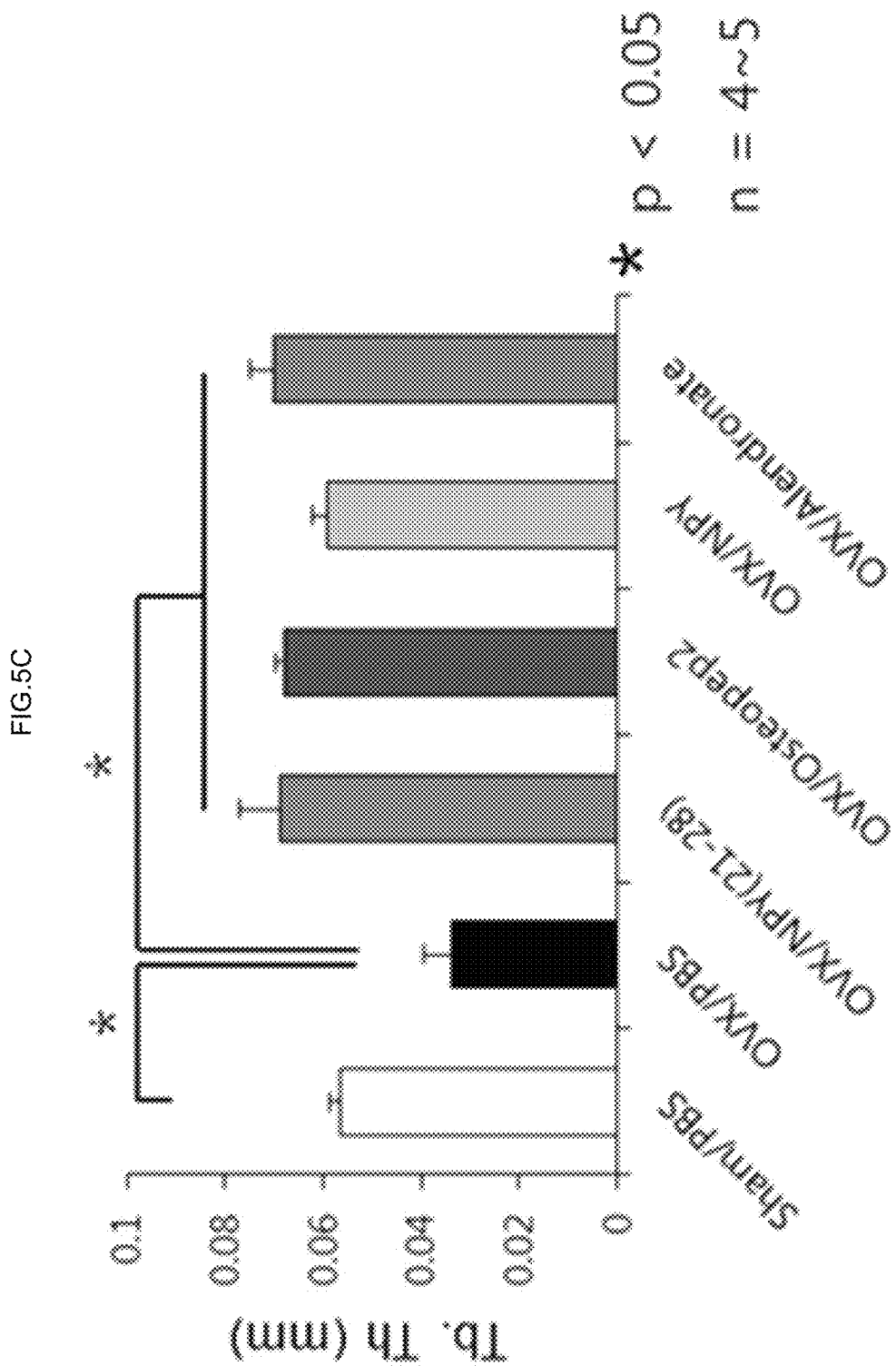

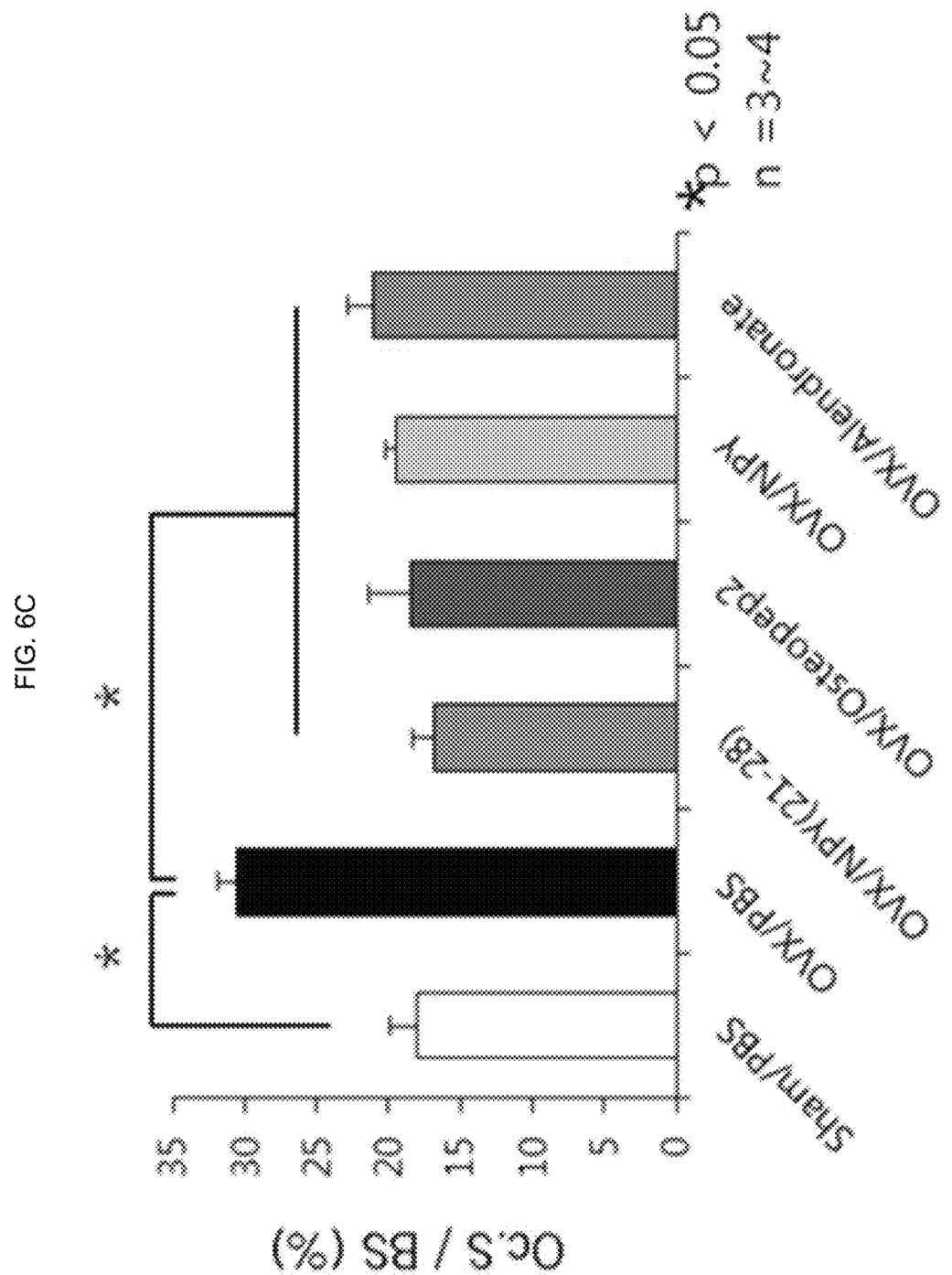

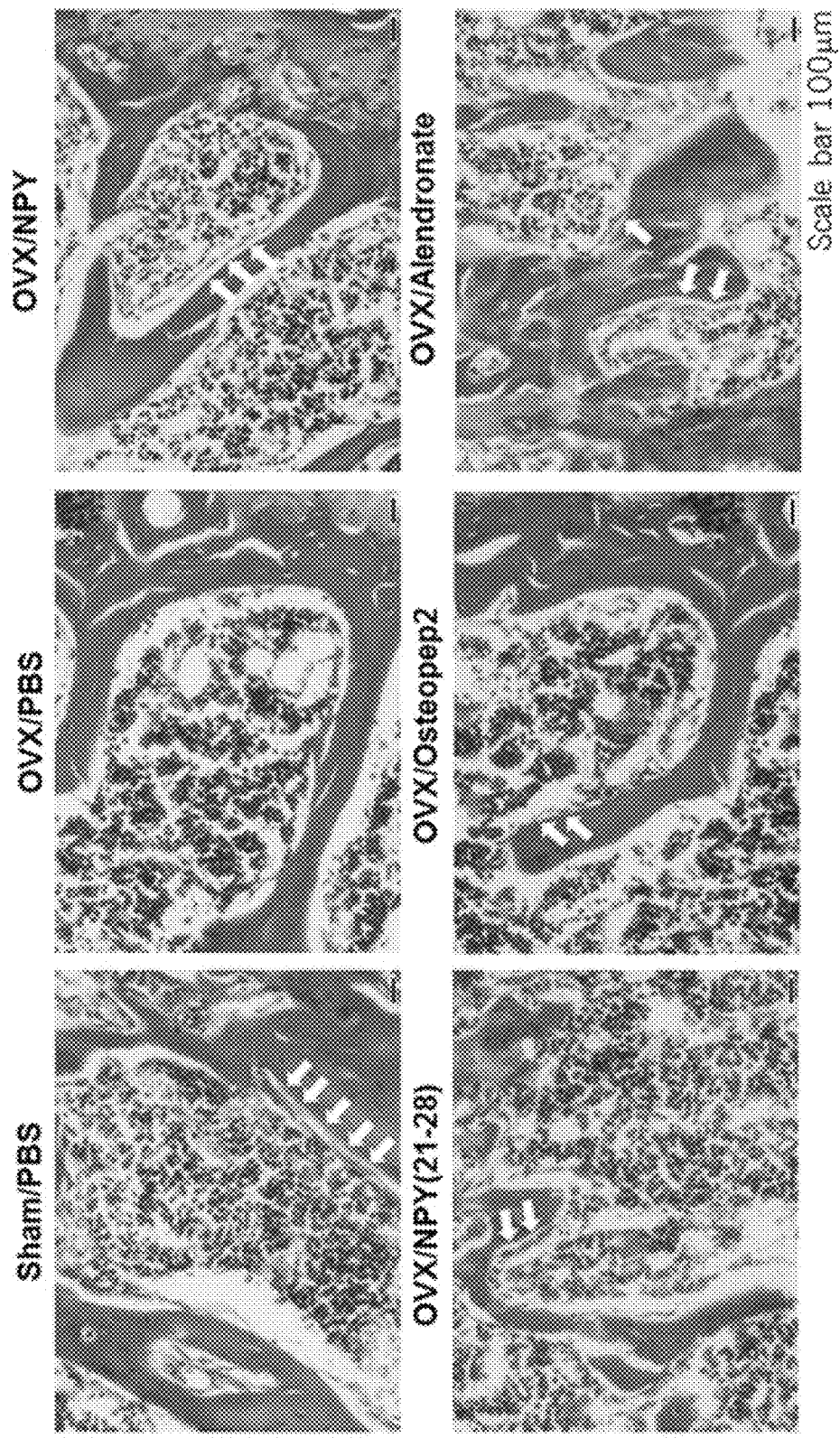

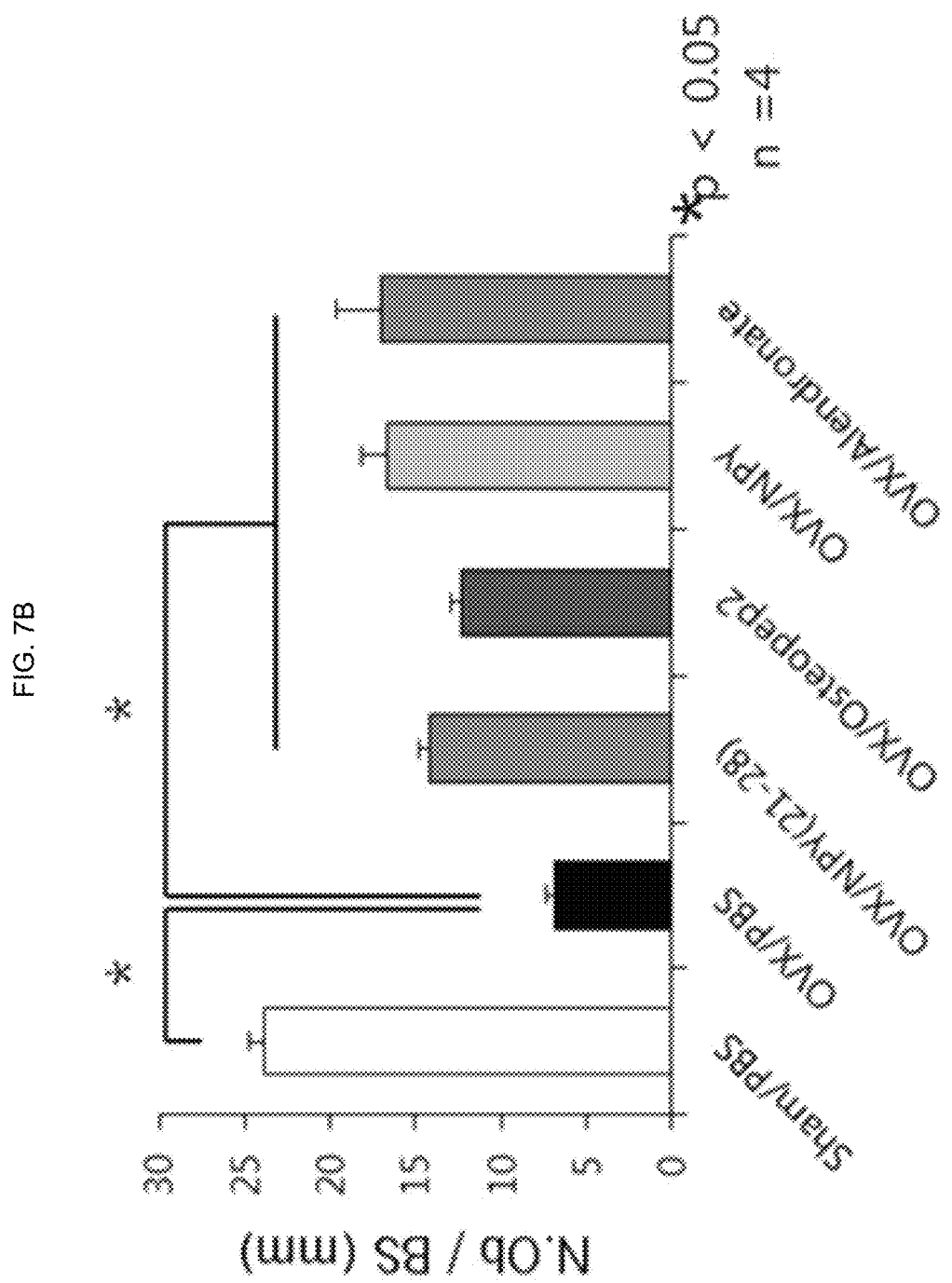

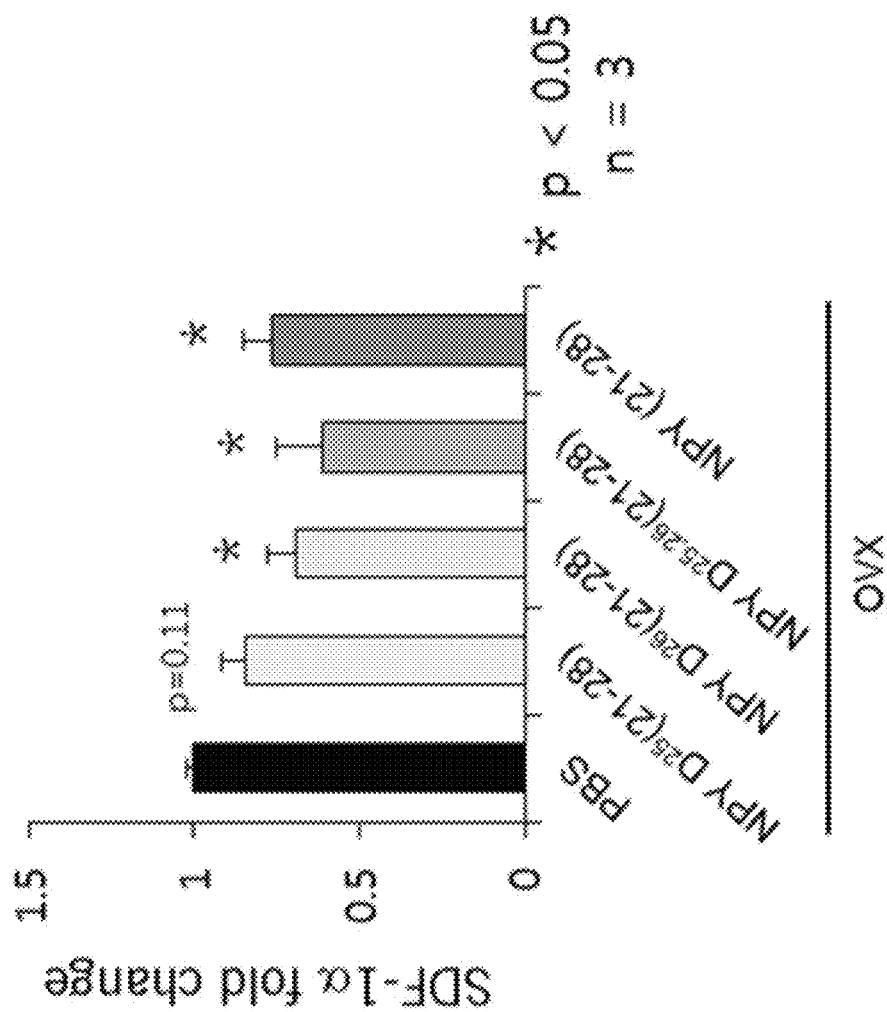

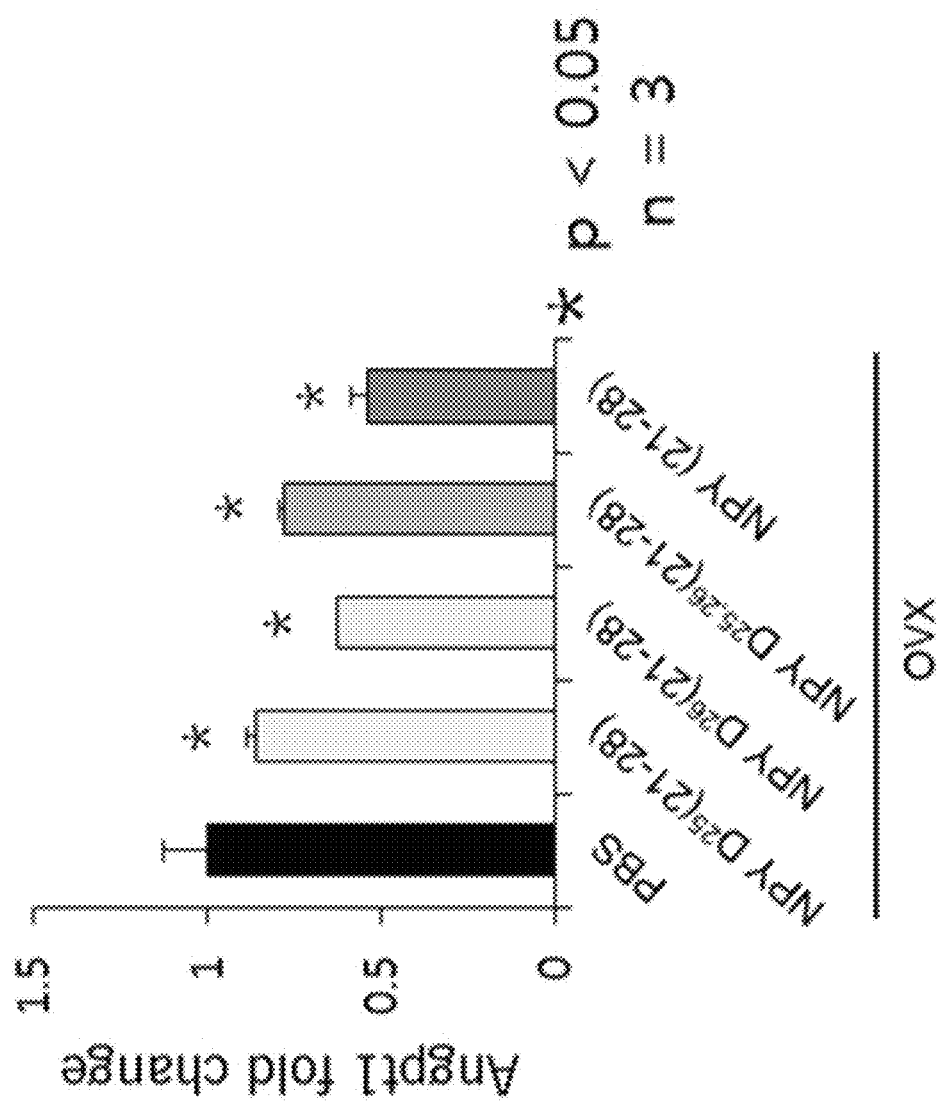

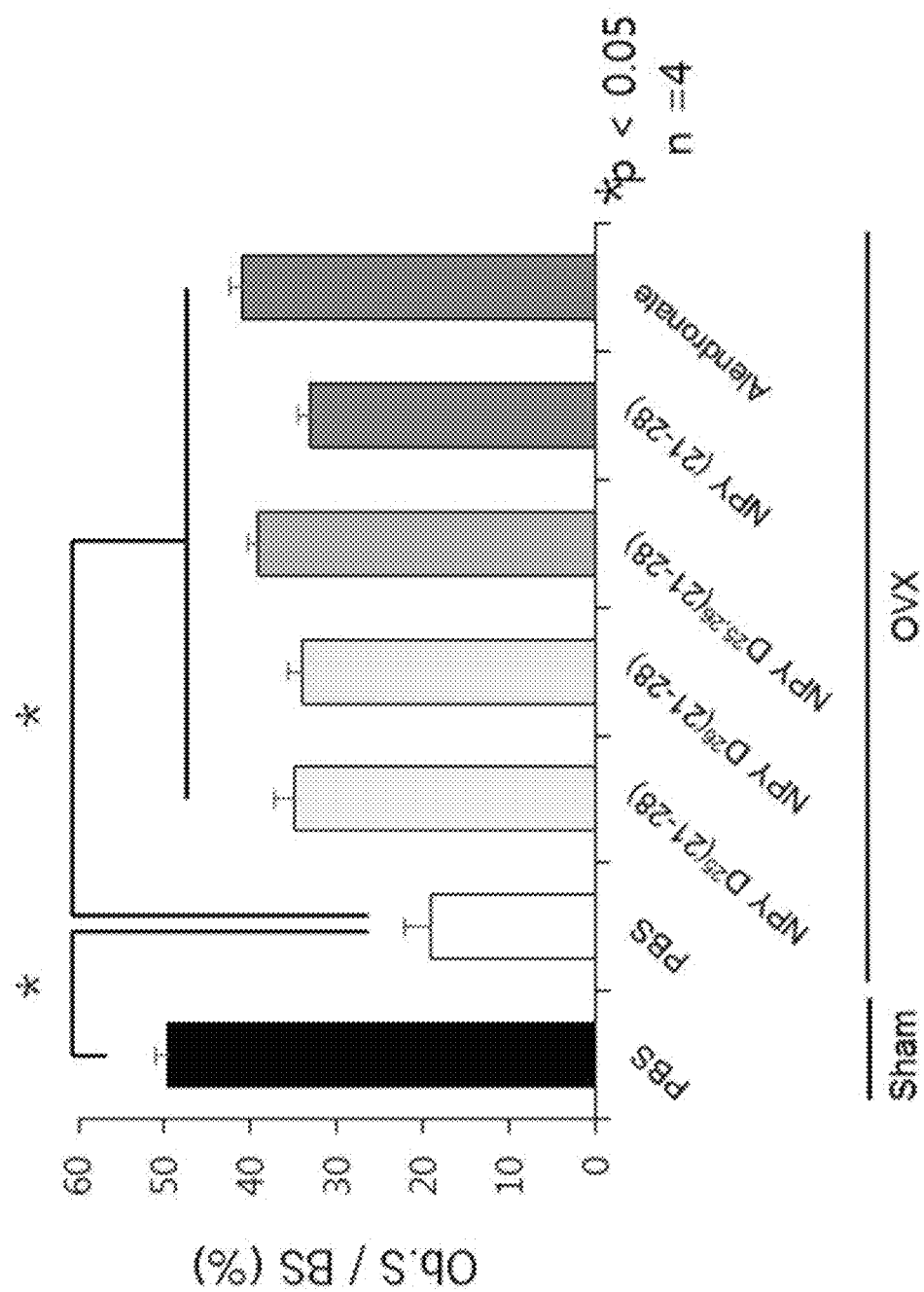

SEQUENCE LISTING

<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: synthetic neuropeptide Y fragment (21-28)

<400> SEQUENCE: 1

Tyr Ser Ala Leu Arg His Tyr Ile
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic neuropeptide Y fragment (24-31)

<400> SEQUENCE: 2

Leu Arg His Tyr Ile Asn Leu Ile
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic neuropeptide Y fragment (29-36)

<400> SEQUENCE: 3

Asn Leu Ile Thr Arg Gln Arg Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic neuropeptide Y fragment (21-28)
<220> FEATURE:
<221> NAME/KEY: Xaa
<222> LOCATION: (5)..(5)
<223> OTHER INFORMATION: Xaa is equal to D-amino acid of Arg

```
<400> SEQUENCE: 4

Tyr Ser Ala Leu Xaa His Tyr Ile
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic neuropeptide Y fragment (21-28)
<220> FEATURE:
<221> NAME/KEY: Xaa
<222> LOCATION: (6)..(6)
<223> OTHER INFORMATION: Xaa is equal to D-amino acid of His

<400> SEQUENCE: 5

Tyr Ser Ala Leu Arg Xaa Tyr Ile
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic neuropeptide Y fragment (21-28)
<220> FEATURE:
<221> NAME/KEY: Xaa
<222> LOCATION: (5)..(5)
<223> OTHER INFORMATION: Xaa is equal to D-amino acid of Arg
<220> FEATURE:
<221> NAME/KEY: Xaa
<222> LOCATION: (6)..(6)
<223> OTHER INFORMATION: Xaa is equal to D-amino acid of His

<400> SEQUENCE: 6

Tyr Ser Ala Leu Xaa Xaa Tyr Ile
1               5

<210> SEQ ID NO 7
<211> LENGTH: 16
<212> TYPE: PRT
<213> ORGANISM: Artificial Sequence
<220> FEATURE:
<223> OTHER INFORMATION: synthetic neuropeptide Y fragment  (21-36)
      (Osteopep2)

<400> SEQUENCE: 7

Tyr Ser Ala Leu Arg His Tyr Ile Asn Leu Ile Thr Arg Gln Arg Tyr
1               5                   10                  15

<210> SEQ ID NO 8
<211> LENGTH: 36
<212> TYPE: PRT
<213> ORGANISM: Artificial Sequence
<220> FEATURE:
<223> OTHER INFORMATION: synthetic neuropeptide Y (NPY)

<400> SEQUENCE: 8

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 9
<211> LENGTH: 21
```

```
<212> TYPE: DNA
<213> ORGANISM: Artificial Sequence
<220> FEATURE:
<223> OTHER INFORMATION: synthetic SDF-1 alpha forward primer

<400> SEQUENCE: 9
ttcctatcag agcccataga g                                              21

<210> SEQ ID NO 10
<211> LENGTH: 20
<212> TYPE: DNA
<213> ORGANISM: Artificial Sequence
<220> FEATURE:
<223> OTHER INFORMATION: synthetic SDF-1 alpha reverse primer

<400> SEQUENCE: 10
ccagaccatc ctggataatg                                                20

<210> SEQ ID NO 11
<211> LENGTH: 23
<212> TYPE: DNA
<213> ORGANISM: Artificial Sequence
<220> FEATURE:
<223> OTHER INFORMATION: synthetic Kit ligand (stem cell factor, SCF)
      forward primer

<400> SEQUENCE: 11
ccaaaagcaa agccaattac aag                                            23

<210> SEQ ID NO 12
<211> LENGTH: 20
<212> TYPE: DNA
<213> ORGANISM: Artificial Sequence
<220> FEATURE:
<223> OTHER INFORMATION: synthetic Kit ligand (stem cell factor, SCF)
      reverse primer

<400> SEQUENCE: 12
agactcgggc ctacaatgga                                                20

<210> SEQ ID NO 13
<211> LENGTH: 18
<212> TYPE: DNA
<213> ORGANISM: Artificial Sequence
<220> FEATURE:
<223> OTHER INFORMATION: synthetic Angiopoietin-1 (Angpt1) forward
      primer

<400> SEQUENCE: 13 acggggtca attctaag                                                   18

<210> SEQ ID NO 14
<211> LENGTH: 18
<212> TYPE: DNA
<213> ORGANISM: Artificial Sequence
<220> FEATURE:
<223> OTHER INFORMATION: synthetic Antiopoietin-1 (Angpt1) reverse
      primer

<400> SEQUENCE: 14
gccattcctg actccaca                                                  18

<210> SEQ ID NO 15
<211> LENGTH: 21
<212> TYPE: DNA
<213> ORGANISM: Artificial Sequence
<220> FEATURE:
```

```
<223> OTHER INFORMATION: synthetic GAPDH forward primer

<400> SEQUENCE: 15
ttgctgttga agtcgcagga g                                              21

<210> SEQ ID NO 16
<211> LENGTH: 20
<212> TYPE: DNA
<213> ORGANISM: Artificial Sequence
<220> FEATURE:
<223> OTHER INFORMATION: synthetic GAPDH reverse primer

<400> SEQUENCE: 16
tgtgtccgtc gtggatctga                                                20
```

NEUROPEPTIDE Y FRAGMENT CAPABLE OF RELEASING HEMATOPOIETIC STEM CELLS INTO BLOOD AND TREATING OSTEOPOROSIS

CROSS-REFERENCE TO RELATED APPLICATIONS

The present application is a continuation of PCT International Patent Application Serial No. PCT/KR2018/007504, filed Jul. 3, 2018, which claims priority from Korean Patent Application No. 10-2017-0085663, filed on Jul. 5, 2017, the entire contents of each of which are incorporated herein by reference.

TECHNICAL FIELD

The present invention relates to a novel peptide exhibiting an effect of releasing myelopoiesis stem cells into blood and an osteoporosis therapeutic effect and use 15 thereof and, in particularly, to the novel peptide consisting of the amino acid sequence of SEQ ID NO: 1, which induces the release of myelopoiesis stem cells into blood to induce a decrease in osteoclasts in the bone marrow and increases the number of osteoblasts and to a pharmaceutical composition comprising the novel peptide as an active ingredient for preventing or treating neutropenia, anemia or osteoporosis.

BACKGROUND OF THE INVENTION

Hematopoietic stem cells refer to cells having the ability to differentiate into blood cells such as red blood cells, white blood cells, and platelets constituting blood. Hematopoietic stem cells are produced in large quantities especially in the bone marrow and present in about 1% of normal bone marrow cells.

However, when the number of hematopoietic stem cells is insufficient, such as aplastic anemia, when hematopoietic stem cells are sick such as leukemia and myelodysplastic syndrome, and when hematopoietic stem cells are damaged by chemotherapy or irradiation, hematopoietic stem cells are unable to function properly and cannot produce blood cells.

In these cases, if the hematopoietic stem cells are completely removed and the normal hematopoietic stem cells are administered to the patient, the hematopoietic stem cells move to the patients bone marrow, and after engraftment, normal blood cells are restored to restore normal hematopoietic function. It is called hematopoietic stem cell transplantation. Source materials that can provide hematopoietic stem cells include bone marrow, umbilical cord blood, and peripheral blood. When hematopoietic stem cell transplantation is performed using each of them, each is called a bone marrow transplant, cord blood transplant, or peripheral blood transplant. The type of transplant is determined by the condition of the patient and the availability of the donor.

Bone marrow is a traditional source of hematopoietic stem cells, but it is sometimes used as a source based on invasive harvesting procedures that require general anesthesia for stem cell donors. During clinical procedures for bone marrow transplantation, the bone is generally a perforated pelvic bone, and the bone marrow cells are drawn out by a syringe.

For clinical transplantation of human hematopoietic stem cells, doctors prefer to collect donor cells from peripheral circulating blood. For decades, small amounts of hematopoietic stem and their progenitor cells circulate in the blood, but over the past decade, researchers found that by injecting cytokines, such as granulocyte leukocyte colony-promoting factor (G-CSF) into donors, the more cells could be induced to migrate from bone marrow to blood. Donors are injected with G-CSF a few days before hematopoietic stem cell collection. Of the cells collected from the donors, about one out of every 100,000 cells in the bone marrow is prolonged hematopoietic stem cells.

Therefore, there is a need to increase the number of hematopoietic stem cells in the blood.

On the other hand, osteoporosis can be classified into postmenopausal osteoporosis, which increase bone resorption with activation of osteoclasts caused by rapid hormonal changes following menopause, and senile osteoporosis, in which osteoblasts decrease due to aging and bone formation decreases. Since osteoporosis fractures lead to severe activity limitations and are associated with a high mortality rate of about 15-35% in hip fractures, the diagnosis and treatment of osteoporosis is important before osteoporotic fractures occur (osteoporosis diagnosis and Treatment Guidelines 2007, 2008).

The prevalence of osteoporosis in Korea has increased threefold over the last five years as of 2008, and it is reported that the annual socioeconomic loss due to osteoporosis fracture is about 1 trillion and 50 billion won (osteoporosis diagnosis and treatment guideline, 2007 and 2008). In addition, according to the latest 2009 national health statistics, the prevalence of osteoporosis within Koreans over 50 and 65 years old is 23.1% and 42.0%, which is very high among chronic diseases. So it is emerging as a big problem for national health (National Health Statistics-National Health and Nutrition Survey, 2009).

Known osteoporosis treatments include bisphosphonate-based drugs. The bisphosphonate are deposited on the mineral components of the bone. When osteoclasts ingurgitate the bisphosphonate-deposited bone, the bisphosphonate forms non-hydrolyzed ATP analogs that are toxic to cells, or causes decreased activity and apoptosis in various ways, resulting in decreased bone resorption and thereby increased bone density. These drugs are known to be relatively safe, but in recent years, there have been concerns that long-term use may affect bone remodeling due to normal bone absorption and bone formation or bone healing process after fracture, which may adversely affect bone strength due to poor elasticity of bone. In fact, it has been reported that this causes stress fractures in many patients.

Therefore, there is an urgent need for the discovery of new bone metabolism mechanisms related to the development of osteoporosis and the development for preventing or treating osteoporosis.

On the other hand, the present inventors have reported that the sympathetic nervous system neuropeptide Y (neuropeptide Y, hereinafter referred to as 'NPY') and fragments thereof have the effect of preventing or treating osteoporosis through prior invention (Korean Patent 10).-1503020, 10-1486061 and 10-1486074). However, the peptides have low stability in the body due to a relatively long length and a high molecular weight, as well as are not economical in terms of time or cost in the preparation of the peptide.

DETAILED DESCRIPTION OF THE INVENTION

Technical Problem

Accordingly, the present inventors have made efforts to solve the above-mentioned problems with the peptides reported in the related art, and as a result of the extensive efforts to develop the peptides that provide better effects for not only preventing or treating osteoporosis, but also promoting the release of hematopoietic stem cells into blood, they have completed the present invention after they have found that a peptide fragment consisting of the 21st to 28th amino acids of the amino acid sequence of NPY was confirmed to have excellent effects for preventing or treating osteoporosis, and promoting the release of hematopoietic stem cells into blood.

Accordingly, an aspect of the present invention is directed to provide a peptide for preventing or treating any one disease selected from the group consisting of neutropenia, anemia and osteoporosis consisting of the amino acid sequence of SEQ ID NO: 1.

An embodiment according to another aspect of the present invention provides a polynucleotide encoding a peptide consisting of the amino acid sequence of SEQ ID NO: 1.

An embodiment according to another aspect of the present invention provides a vector comprising the polynucleotide.

An embodiment according to another aspect of the present invention provides a host cell transformed with the vector.

An embodiment according to another aspect of the present invention provides a pharmaceutical composition for preventing or treating any one disease selected from the group consisting of neutropenia, anemia and osteoporosis comprising a peptide consisting of the amino acid sequence of SEQ ID NO: 1 as an active ingredient.

An embodiment according to another aspect of the present invention provides a pharmaceutical composition for preventing or treating any one disease selected from the group consisting of neutropenia, anemia and osteoporosis consisting of a peptide consisting of the amino acid sequence of SEQ ID NO: 1.

An embodiment according to another aspect of the present invention provides a pharmaceutical composition for preventing or treating any one disease selected from the group consisting of neutropenia, anemia and osteoporosis consisting essentially of the peptide consisting of the amino acid sequence of SEQ ID NO: 1 as an active ingredient.

An embodiment according to another aspect of the present invention provides a food composition for preventing or improving any one disease selected from the group consisting of neutropenia, anemia and osteoporosis comprising a peptide consisting of the amino acid sequence of SEQ ID NO: 1 as an active ingredient.

An embodiment according to another aspect of the present invention provides a food composition for preventing or improving any one disease selected from the group consisting of neutropenia, anemia and osteoporosis consisting of a peptide consisting of the amino acid sequence of SEQ ID NO: 1.

An embodiment according to another aspect of the present invention provides a food composition for preventing or improving any one disease selected from the group consisting of neutropenia, anemia and osteoporosis consisting essentially of a peptide consisting of the amino acid sequence of SEQ ID NO: 1 as an active ingredient.

Still further aspect of the present invention is to provide a use of a peptide consisting of the amino acid sequence of SEQ ID NO: 1 for preparing a therapeutic agent for treating any one disease selected from the group consisting of neutropenia, anemia and osteoporosis.

Still further aspect of the present invention is to provide a method for treating any one disease selected from the group consisting of neutropenia, anemia and osteoporosis, the method comprising administering an effective amount of a composition to a subject in need thereof, wherein the composition comprises the peptide consisting of the amino acid sequence of SEQ ID NO: 1 as an active ingredient.

Technical Solution

An embodiment according to an aspect of the present invention provides a peptide for preventing or treating any one disease selected from the group consisting of neutropenia, anemia and osteoporosis consisting of the amino acid sequence of SEQ ID NO: 1.

An embodiment according to an aspect of the present invention provides a polynucleotide encoding a peptide consisting of the amino acid sequence of SEQ ID NO: 1.

An embodiment according to an aspect of the present invention provides a vector comprising the polynucleotide.

An embodiment according to an aspect of the present invention provides a host cell transformed with the vector.

An embodiment according to an aspect of the present invention provides a pharmaceutical composition for preventing or treating any one disease selected from the group consisting of neutropenia, anemia and osteoporosis comprising the peptide of the present invention as an active ingredient.

An embodiment according to an aspect of the present invention provides a pharmaceutical composition for preventing or treating any one disease selected from the group consisting of neutropenia, anemia and osteoporosis consisting of the peptide of the present invention.

An embodiment according to another aspect of the present invention provides a pharmaceutical composition for preventing or treating any one disease selected from the group consisting of neutropenia, anemia and osteoporosis consisting essentially of the peptide of the present invention as an active ingredient.

An embodiment according to another aspect of the present invention provides a food composition for preventing or improving any one disease selected from the group consisting of neutropenia, anemia and osteoporosis comprising the peptide of the present invention as an active ingredient.

An embodiment according to another aspect of the present invention provides a food composition for preventing or improving any one disease selected from the group consisting of neutropenia, anemia and osteoporosis consisting of the peptide of the present invention.

An embodiment according to still another aspect of the present invention provides a food composition for preventing or improving any one disease selected from the group consisting of neutropenia, anemia and osteoporosis consisting essentially of the peptide of the present invention as an active ingredient.

An embodiment according to still another aspect of the present invention provides a use of a peptide consisting of the amino acid sequence of SEQ ID NO: 1 for preparing a therapeutic agent for treating any one disease selected from the group consisting of neutropenia, anemia and osteoporosis.

An embodiment according to still further aspect of the present invention provides a method for treating any one disease selected from the group consisting of neutropenia, anemia and osteoporosis, the method comprising administering an effective amount of a composition to a subject in need thereof, wherein the composition comprises the peptide consisting of the amino acid sequence of SEQ ID NO: 1 as an active ingredient.

Hereinafter, the present invention will be described in detail.

The present invention provides a peptide for preventing or treating any one disease selected from the group consisting of neutropenia, anemia and osteoporosis consisting of the amino acid sequence of SEQ ID NO: 1.

The peptide of SEQ ID NO: 1 of the present invention is a peptide fragment consisting of 21 to 28 amino acids of the amino acid sequence of neuropeptide Y (NPY) (NPY (21-28)), and the peptide consists of the amino acid sequence of Tyr-Ser-Ala-Leu-Arg-His-Tyr-Ile.

The peptide represented by the amino acid sequence of SEQ ID NO: 1 of the present invention is composed of a total of eight amino acids. Because the peptide has a very short sequence, there is no side effect, excellent efficacy and relatively low production cost.

That is, since the peptide of the present invention has a very short amino acid sequence, it can minimize immunogenicity and toxic side effects, and since the molecular weight is small, it can be easily synthesized, which makes mass production easy and brings cost-effectiveness. In addition, the small molecular weight has the advantage of being able to cross tissue barriers more quickly.

According to an example of the present invention, within the amino acid sequence of NPY adjacent to the peptide of SEQ ID NO: 1 of the present invention, two other peptide fragments consisting of eight amino acids did not show the effect for preventing or treating any osteoporosis, but the peptide of the present invention showed a better effect than NPY and its 21st to 36th amino acid fragments (Osteopep2) used as a positive control. That is, the peptide of SEQ ID NO: 1 of the present invention can be said to consist of only the core fragments showing pharmacological activity in the amino acid sequence of NPY and/or Osteopep2. Because of the short length of the peptide, the above-mentioned advantages appear, and thus, it can be determined that a better effect for preventing or treating osteoporosis has been shown.

According to an example of the present invention, the present inventors modified the structure of some amino acids to improve the affinity to the receptor of the peptide having the amino acid sequence of SEQ ID NO: 1. That is, as a result of preparing a peptide in which the 5th amino acid arginine and/or the 6th amino acid histidine of the amino acid sequence of SEQ ID NO: 1 was transformed to D-type, and evaluating an effect for preventing or treating osteoporosis, it was confirmed that the peptide shows a better effect than NPY (21-28) as well as Osteopep2 and NPY.

Accordingly, the present invention provides a peptide, wherein at least one amino acid selected from the group consisting of the fifth and sixth amino acids of the amino acid sequence of SEQ ID NO: 1 is D-type.

The peptide of the present invention is understood as a concept including a functional equivalent of a peptide having the amino acid sequence of SEQ ID NO: 1. "Functional equivalent" means a peptide that exhibits substantially homogeneous physiological activity with the peptide of SEQ ID NO: 1. "Homogeneous physiological activity" refers to having an isomerizing capacity and having at least 60% or more amino acid sequence homology, preferably 70%, more preferably 90% or more. "Functional equivalents" also include amino acid sequence variants in which some or all of the amino acids of a natural protein are substituted, or some of the amino acids are deleted or added. Substitutions of the amino acids are preferably conservative substitutions. Examples of conservative substitutions of amino acids present in nature are as follows; Aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met).

The peptide of the present invention can be prepared by a method known to those skilled in the art. Such peptides can often be produced in prokaryotic or eukaryotic cells by expressing the polynucleotides encoding the peptide sequences of the invention as part of a larger polypeptide. Alternatively, such peptides can be synthesized by chemical methods. Methods for expression of heterologous proteins in recombinant hosts, chemical synthesis of polypeptides and in vitro transcription are well known in the art. It is further described in references (references: Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11: 255; Kaiser et al. (1989) Ann. Rev. Biochem. 57:957; and Offord, R. E. (1980) Semisynthetic Proteins, Wiley Publishing).

The present invention provides a pharmaceutical composition for preventing or treating any one disease selected from the group consisting of neutropenia, anemia and osteoporosis comprising a peptide consisting of the amino acid sequence of SEQ ID NO: 1 or a peptide in which the fifth and/or sixth amino acid thereof is modified to D-type as an active ingredient.

In addition, the present invention provides a pharmaceutical composition for preventing or treating any one disease selected from the group consisting of neutropenia, anemia and osteoporosis consisting of a peptide consisting of the amino acid sequence of SEQ ID NO: 1 or a peptide in which the fifth and/or sixth amino acid thereof is modified to D-type.

In addition, the present invention provides a pharmaceutical composition for preventing or treating any one disease selected from the group consisting of neutropenia, anemia and osteoporosis consisting essentially of a peptide consisting of the amino acid sequence of SEQ ID NO: 1 or a peptide in which the fifth and/or sixth amino acid thereof is modified to D-type as an active ingredient.

According to an example of the present invention, the peptide of the present invention was confirmed that the effect of promoting the release of hematopoietic stem cells into blood by inhibiting the expression of adhesion factors of hematopoietic stem cells. Since hematopoietic stem cells released into the blood have the ability to differentiate into blood cells such as red blood cells, white blood cells and platelets, the peptide of the present invention exhibits the effect for preventing or treating neutropenia and anemia caused by various causes.

In the present invention, the cause of the neutropenia is not particularly limited, and preferably, it may be due to any one or more causes selected from the group consisting of radiation, alcoholism, drugs, allergic diseases, aplastic anemia, autoimmune diseases, T-γ lymphocyte proliferative diseases (T-γ) LPD), myelodysplasia, myeloid fibrosis, dysgammaglobulinemia, paroxysmal nocturnal hemoglobinuria, cancer, vitamin B12 deficiency, folate deficiency, viral infection, bacterial infection, spleen disease, hemodialysis, or transplantation, leukemia, myeloma, lymphoma, metastatic solid tumors that infiltrate and replace the bone marrow, toxins, bone marrow failure, Schwarzmann-Diamond syndrome, cartilage-hair dysfunction, congenital dyskeratosis and type I B glycogen storage disease.

Since the peptide of the present invention has an effect of promoting the release of hematopoietic stem cells from bone marrow into blood, a pharmaceutical composition could be used for releasing donor myelopoiesis stem cells into peripheral blood in preparation for transplantation of hematopoietic stem cells.

Hematopoietic Stem Cell Transplantation means a method used to fundamentally treat these diseases when abnormalities occur in the process of cell differentiation, such as leukemia, or when the number of hematopoietic stem cells decreases, such as aplastic anemia. Hematopoietic stem cell transplantation can be classified into bone marrow hematopoietic stem cell transplant derived from bone marrow according to the source of hematopoietic stem cells, peripheral blood hematopoietic stem cell transplant derived from peripheral blood after administration of anticancer agent or leukocyte structure growth factor, and cord blood hematopoietic stem cell transplantation from placenta. The hematopoietic stem cell transplant in the present invention preferably means peripheral blood hematopoietic stem cell transplantation.

That is, the peptide of the present invention can be used as a treatment for neutropenia of cancer patients undergoing chemotherapy and radiation, neutropenia due to aplastic anemia, congenital and idiopathic neutropenia, neutropenia due to infectious diseases, neutropenia caused by autoimmune diseases. In addition, it may be used to promote releasing donor myelopoiesis stem cells into peripheral blood for hematopoietic stem cell transplantation.

According to another example of the present invention, the peptide of the present invention was confirmed to have an excellent effect for preventing or treating osteoporosis. On the other hand, the effect for preventing or treating osteoporosis of the peptide of the present invention was found to inhibit the reduction in bone density and bone tissue thickness of osteoporosis mice by reducing the number of osteoclasts that differentiate from hematopoietic stem cells in the bone marrow and by simultaneously increasing the number of osteoblasts after inducing the release of myelopoiesis stem cells into blood.

That is, the effect of promoting the release of myelopoiesis stem cells into blood represented by the peptide of the present invention not only acts as a mechanism for treating neutropenia and anemia, but also as a mechanism for treating osteoporosis.

The composition of the present invention may further comprise a pharmaceutically acceptable additive, and the pharmaceutically acceptable additives may include starch, gelatinized starch, microcrystalline cellulose, lactose, povidone, colloidal silicon dioxide, calcium hydrogen phosphate, lactose, mannitol, malt, gum arabic, pregelatinized starch, corn starch, powdered cellulose, hydroxypropyl cellulose, opadry, sodium starch glycolate, lead carnauba, synthetic aluminum silicate, stearic acid, magnesium stearate, aluminum stearate, calcium stearate, white sugar, dextrose, sorbitol, and talc. The pharmaceutically acceptable additive according to the present invention is preferably included in 0.1 to 90 parts by weight based on the composition, but is not limited thereto.

In addition, the composition of the present invention may be administered in various oral and parenteral dosage forms in actual clinical administration, and when formulated, it may be prepared using diluents or excipients such as commonly used fillers, extenders, binders, wetting agents, disintegrating agents, and surfactants.

Solid agents for oral administration include tablets, pills, powders, granules, and capsules. Such solid agents may be prepared by mixing at least one excipient such as starch, calcium carbonate, sucrose, lactose or gelatin with a peptide having the amino acid sequence of SEQ ID NO: 1. In addition to simple excipients, lubricants such as magnesium stearate talc may also be used. Oral liquid agents include suspensions, solvents, emulsions and syrups. In addition to commonly used simple diluents such as water and liquid paraffin, various excipients may be included such as wetting agents, sweetening agents, fragrances, and preservatives.

Agents for parenteral administration may include sterile aqueous solutions, non-aqueous solvents, suspensions, emulsions, lyophilized agents, and suppositories. As the non-aqueous solvent and the suspension solvent, propylene glycol, polyethylene glycol, vegetable oils such as olive oil, and injectable esters such as ethyl oleate can be used. As the base of the suppository, witepsol, macrogol, tween 61, cacao butter, laurinum, and glycerogelatin can be used.

Injections may include conventional additives such as solubilizers, isotonic agents, suspending agents, emulsifiers, stabilizers, and preservatives.

In addition, the compositions of the present invention may further include any physiologically acceptable carrier, excipient or stabilizer (Remington: The Science and Practice of Pharmacy, 19th Edition, Alfonso, R., ed, Mack Publishing Co. (Easton, Pa.: 1995). The acceptable carriers, excipients or stabilizers are nontoxic to recipients at the dosages and concentrations employed, and include buffer solution such as phosphoric acid, citric acid and other organic acids; Antioxidants including ascorbic acid; Low molecular weight (less than about 10 residues) polypeptides; Proteins such as serum albumin, gelatin or immunoglobulins; Hydrophilic polymers such as polyvinylpyrrolidone; Amino acids such as glycine, glutamine, asparagine, arginine or lysine; Monosaccharides, disaccharides, and other carbohydrates including glucose, mannose, or dextrins; Chelating agents such as EDTA; Sugar alcohols such as mannitol or sorbitol; Salt-forming counterions such as sodium; And/or nonionic surfactants such as tween, pluronics or polyethylene glycol (PEG).

The dosage of the pharmaceutical composition of the present invention to the human body may vary depending on the age, weight, sex, injection type, health condition and degree of disease of the patient, and is generally 0.01-100 mg/kg/day, preferably 0.1-20 mg/kg/day, more preferably 1-5 mg/kg/day, but is not limited thereto. In addition, divided doses may be administered at regular intervals according to the judgment of a doctor or a pharmacist.

The present invention also provides a food composition for preventing or improving osteoporosis comprising a peptide consisting of the amino acid sequence of SEQ ID NO: 1 as an active ingredient.

The food composition according to the present invention includes all forms such as functional food, nutritional supplement, health food, and food additives. These types can be prepared in various forms according to conventional methods known in the art.

For example, as the health food, the food composition itself of the present invention may be prepared in the form of tea, juice and drink for drinking, or may be ingested by granulation, encapsulation and powdering. In addition, the food composition of the present invention may be prepared in the form of a composition by mixing with a known substance or active ingredient known to have an effect for preventing or treating osteoporosis.

As the functional food, it can also manufacture by adding the food composition of this invention to beverages (including alcoholic beverages), fruits and processed foods (e.g., canned fruit, canned foods, jams, and marmalade), fish, meat and processed foods (e.g., ham, sausage corn beef, etc.), breads and noodles (e.g., udon, soba, ramen, spaghetti, and macaroni), fruit juices, various drinks, cookies, malts, dairy products (e.g., butter and cheese), edible vegetable oils, margarine, vegetable protein, retort food, frozen food, and various seasonings (e.g., miso, soy sauce and sauce).

The preferred content of the food composition according to the present invention is not limited thereto, but is preferably 0.01 to 50% by weight of the total weight of the finally prepared food. In order to use the food composition of the present invention in the form of a food additive, it may be prepared and used in powder or concentrate form.

The present invention provides a polynucleotide encoding the peptide.

The "polynucleotide" is a polymer of deoxyribonucleotides or ribonucleotides present in single- or double-stranded form. It includes RNA genomic sequences, DNA (gDNA and cDNA) and RNA sequences transcribed therefrom, and include analogs of natural polynucleotides unless specifically stated otherwise.

The polynucleotide includes not only the nucleotide sequence encoding the peptide, but also a sequence complementary to the sequence. The complementary sequence includes not only a perfectly complementary sequence, but also a substantially complementary sequence. This means a sequence capable of hybridizing with the nucleotide sequence encoding the peptide of SEQ ID NO: 1 under stringent conditions known in the art.

The polynucleotide may also be modified. Such modifications include addition, deletion or non-conservative substitutions or conservative substitutions of nucleotides.

The polynucleotide encoding the amino acid sequence includes a nucleotide sequence showing substantial identity to the nucleotide sequence. The substantial identity may be a sequence that exhibits at least 80% homology, at least 90% homology, or at least 95% homology when aligning the nucleotide sequence and any other sequence to the maximum correspondence, and analyzing the aligned sequence using algorithms commonly used in the art.

The present invention provides a vector comprising the polynucleotide.

The term "vector" means a means for expressing a gene of interest in a host cell. For example, viral vectors such as plasmid vectors, cosmid vectors and bacteriophage vectors, adenovirus vectors, retrovirus vectors, and adeno-associated virus vectors are included. Vectors that can be used as the recombinant vector can be produced by engineering plasmids (e.g., pSC101, pGV1106, pACYC177, ColE1, pKT230, pME290, pBR322, pUC8/9, pUC6, pBD9, pHC79, plJ61, pLAFR1, pHV14, pGEX series, pET series and pUC19), phage (e.g., λgt4λB, λ-Charon, λΔz1 and M13) or viruses (e.g., CMV and SV40) often used in the art.

The polynucleotide encoding the amino acid sequence of SEQ ID NO: 1 in the recombinant vector may be operably linked to a promoter. The term "operatively linked" means a functional link between a nucleotide expression control sequence (e.g., a promoter sequence) and another nucleotide sequence. Thus, the regulatory sequence can thereby regulate transcription and/or translation of the other nucleotide sequence. The recombinant vector can typically be constructed as a vector for cloning or a vector for expression. The expression vector may be a conventional one used in the art to express foreign proteins in plants, animals or microorganisms. The recombinant vector may be constructed through various methods known in the art.

The recombinant vector may be constructed using prokaryotic or eukaryotic cells as hosts. For example, when the vector used is an expression vector and the prokaryotic cell is a host, a strong promoter (for example, a pLλ promoter, trp promoter, lac promoter, tac promoter and T7 promoter) capable of promoting transcription generally includes ribosome binding sites and transcription/translation termination sequences for initiation of translation. In the case of using a eukaryotic cell as a host, replication origins that operate in the eukaryotic cells include f1 replication origin, SV40 replication origin, pMB1 replication origin, adeno replication origin, AAV replication origin, CMV replication origin, and BBV replication origin, but are not limited thereto. In addition, promoters derived from the genome of mammalian cells (e.g., metallothionine promoters) or promoters derived from mammalian viruses (e.g., adenovirus late promoters, vaccinia virus 7.5K promoters, SV40 promoters, Cytomegalovirus (CMV) promoter and tk promoter of HSV) can be used and generally have a polyadenylation sequence as a transcription termination sequence.

The present invention provides a host cell transformed with the vector.

The host cell may use any host cell known in the art, and prokaryotic cells include, for example, *E. coli* JM109, *E. coli* BL21, *E. coli* RR1, *E. coli* LE392, *E. coli* B, *E. coli* X 1776, *E. coli* W3110, Strains of the genus *Bacillus*, such as *Bacillus subtilis, Bacillus thuringiensis*, and enterobacteria and strains, such as *Salmonella typhimurium, Serratia marsonsons*, and various *Pseudomonas* species. As a host cell in the case of transformation into eukaryotic cells, yeast (*Saccharomyce cerevisiae*), insect cells, plant cells, and animal cells such as SP2/0, CHO (Chinesehamster ovary) K1, CHO DG44, PER.C6, W138, BHK, COS-7, 293, HepG2, Huh7, 3T3, RIN and MDCK cell lines can be used.

The present invention provides a method for preparing a peptide for preventing or treating osteoporosis, the method comprising culturing the host cell.

Insertion of the polynucleotide or a recombinant vector comprising the same into a host cell may employ an insertion method well known in the art. As the insertion method, for example, when the host cell is a prokaryotic cell, a $CaCl_2$ method or an electroporation method may be used. When the host cell is a eukaryotic cell, micro-injection, calcium phosphate precipitation, electroporation, liposome-mediated transfection and gene bombardment may be used, but are not limited thereto. When using microorganisms such as *E. coli*, productivity is higher than that of animal cells, but they are not suitable for the production of intact Ig antibodies due to glycosylation problems. However, they can be used for the production of antigen-binding fragments such as Fab and Fv.

The method for selecting the transformed host cell can be easily carried out according to methods well known in the art using a phenotype expressed by a selection label. For example, when the selection marker is a specific antibiotic resistance gene, the transformant can be easily selected by culturing the transformant in a medium containing the antibiotic.

The present invention provides a use of a peptide consisting of the amino acid sequence of SEQ ID NO: 1 for preparing a therapeutic agent for any one of the diseases selected from the group consisting of neutropenia, anemia and osteoporosis.

The present invention provides a method for treating any one disease selected from the group consisting of neutropenia, anemia and osteoporosis, the method comprising administering an effective amount of a composition to a subject in need thereof, wherein the composition comprises the peptide consisting of the amino acid sequence of SEQ ID NO: 1 as an active ingredient.

The 'effective amount' of the present invention, when administered to a subject, refers to an amount that has not only an effect of improving, treating, preventing, detecting, diagnosing neutropenia, anemia or osteoporosis, but also an effect of inhibiting or reducing neutropenia, anemia or osteoporosis. The 'subject' may be an animal, preferably an animal including a mammal, especially a human, and may be a cell, tissue, or organ derived from the animal. The subject may be a patient in need of the effect.

The term 'treatment' of the present invention refers generically to ameliorating the symptoms of neutropenia, anemia, osteoporosis or neutropenia, anemia, osteoporosis and is intended to treat, substantially prevent, or ameliorate such these diseases. It may include alleviating, treating or preventing one or most of the symptoms resulting from neutropenia, anemia or osteoporosis, but is not limited thereto.

The term 'comprising' of the present invention is used in the same way as 'containing' or 'characteristic' and does not exclude additional component elements or method steps not mentioned in the composition or method. The term 'consisting of' means to exclude additional elements, steps or components, unless otherwise noted. The term "essentially consisting of" means within the range of the composition or method, including the component elements or steps described, as well as the component elements or steps that do not substantially affect its basic properties.

Effects of the Invention

The peptide consisting of the amino acid sequence of SEQ ID NO: 1 of the present invention effectively induces releasing hematopoietic stem cells into blood by reducing the expression level of hematopoietic stem cell adhesion factors in bone marrow. This induces a decrease in the number of osteoclasts in bone marrow and an increase in the number of osteoblasts, and has the effect of alleviating the decrease in bone density. Therefore, the peptide consisting of the amino acid sequence of SEQ ID NO: 1 of the present can be very usefully used for the development of a prophylactic or therapeutic agent for osteoporosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A to 3C are a result showing the expression levels of adhesion factors of hematopoietic stem cell in bone marrow with fold change compared to the control group after administration of each peptide to the animal models of osteoporosis (OVX: osteoporosis animal models with ovarian resection after subcutaneous incision).

FIG. 4A shows the number of myelopoiesis progenitor cells in the blood after administration of each peptide in the animal models of osteoporosis.

FIGS. 5A to 5C show the results of micro-CT imaging the overall bone density after administration of each peptide to animal models of osteoporosis (5A), and then graphically quantifying the change of bone density (5B) and the change of bone tissue thickness (5C) (Sham: control animal models with subcutaneous incision only, OVX: osteoporosis with ovarian resection after subcutaneous incision).

FIGS. 6A to 6C show the results of TRAP staining the change in the number of osteoclasts in bone marrow after administration of each peptide to animal models of osteoporosis (6A), and then graphically quantifying the number of osteoclasts (6B) and the surface area occupied by osteoclasts (6C) (Sham: control animal models with subcutaneous incision only, OVX: osteoporosis animal model with ovarian resection after subcutaneous incision).

FIGS. 7A to 7C show the results of H & E staining of changes in osteoblasts in bone marrow after administration of each peptide to animal models of osteoporosis (7A), and then graphically quantifying the number of osteoblasts (7B) and the surface area occupied by osteoblasts (7C) (Sham: control animal model with subcutaneous incision only, OVX: osteoporosis animal models with ovarian resection after subcutaneous incision).

FIGS. 10A to 10C are a result showing the expression levels of adhesion factors of hematopoietic stem cell in bone marrow with fold change compared to the control group after administration of each peptide to the animal models of osteoporosis (OVX: osteoporosis animal models with ovarian resection after subcutaneous incision).

FIGS. 14A to 14C show the results of H & E staining of changes in osteoblasts in bone marrow after administration of each peptide to animal models of osteoporosis (14A), and then graphically quantifying the number of osteoblasts (14B) and the surface area occupied by osteoblasts (14C) (Sham: control animal model with subcutaneous incision only, OVX: osteoporosis animal models with ovarian resection after subcutaneous incision).

MODE FOR CARRYING OUT INVENTION

Figure 1A:
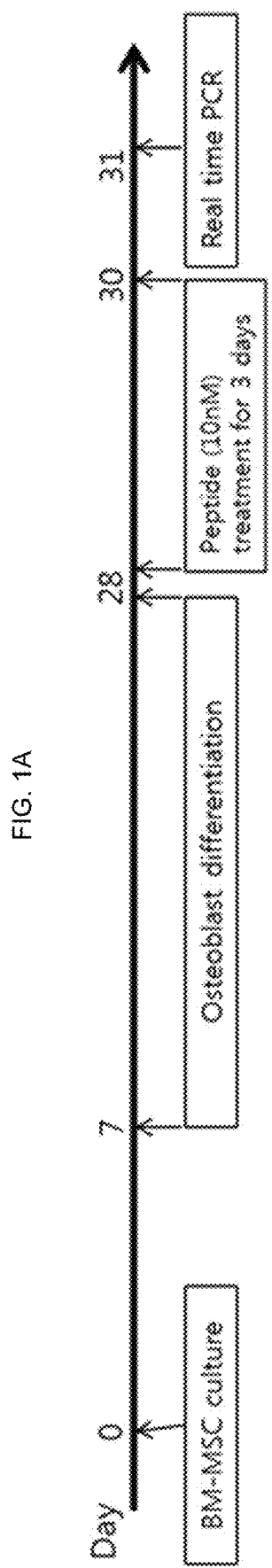
FIGS. 1A to 1D are a result showing the change in the expression levels of the adhesion factors after treating the three kinds of recombinant peptides, NPY(21-28), NPY(24-31), and NPY(29-36), to osteoblasts that express adhesion factors of myelopoiesis stem cells (1A: summary of the experiment, 1B to 1D: a graph showing the expression levels of adhesion factors with fold change relative to the control group).
Figure 1B:
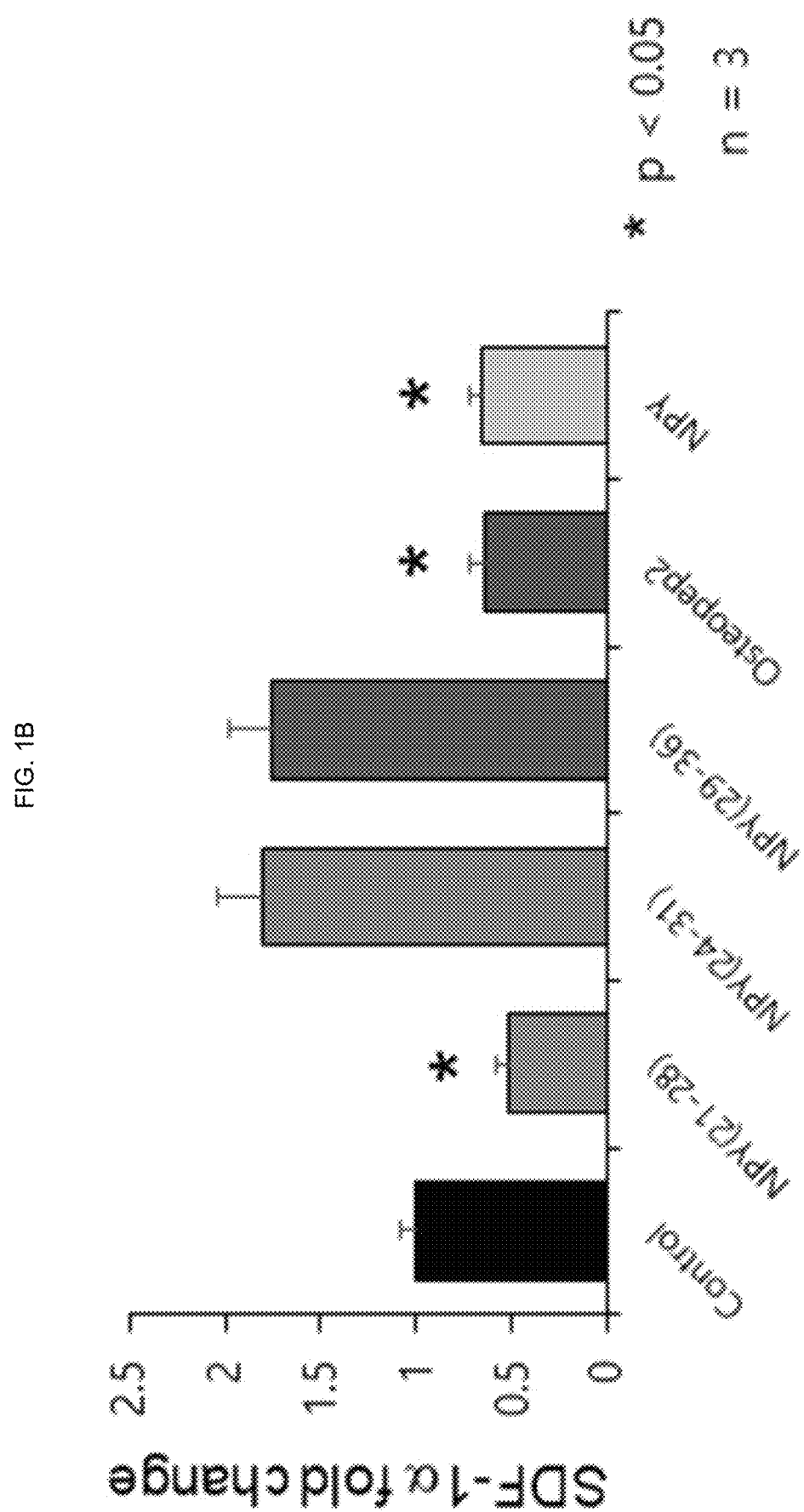
Figure 1C:
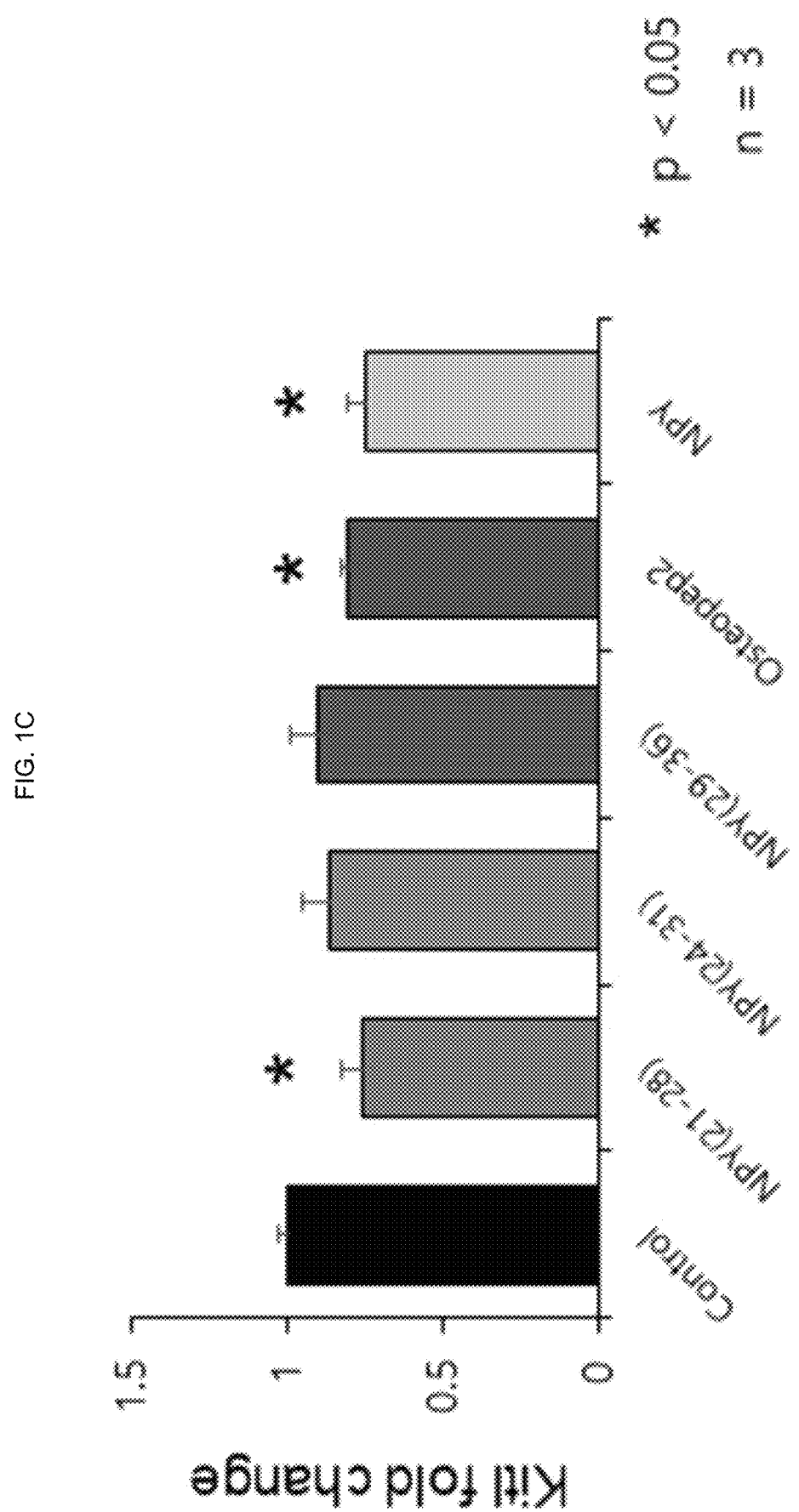
Figure 1D:
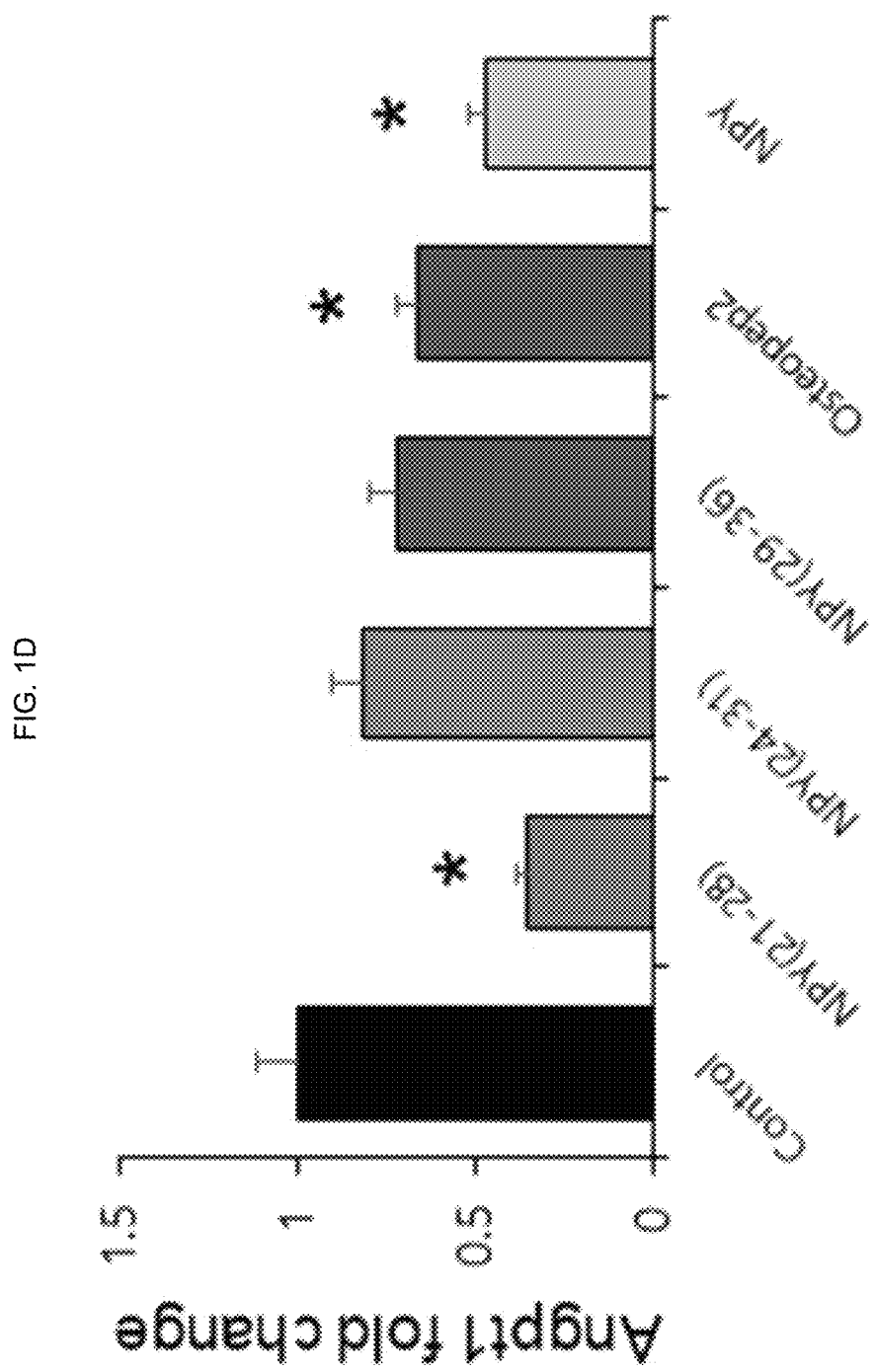

Hereinafter, the present invention will be described in detail.

However, the following examples are illustrative of the present invention, and the present invention is not limited to the following examples.

Example 1. Experimental Materials and Experimental Methods 1-1. Mouse Preparation and Drug Treatment Protocols All mice used in the experiment were 6 to 8 weeks old mice, C57BL/6 mice, and purchased from Jackson Laboratory (Bar Harbor, Me., USA). NPY (21-28) (SEQ ID NO: 1), NPY (24-31) (SEQ ID NO: 2), NPY (29-36) (SEQ ID NO: 3), NPY D25 (21-28) (SEQ ID NO: 4), NPY D26 (21-28) (SEQ ID NO: 5), NPY D25, 26 (21-28) (SEQ ID NO: 6), NPY (21-36) (Osteopep2) (SEQ ID NO: 7) were prepared from Anygen. Full length NPY (SEQ ID NO: 8) was purchased from Bachem. 10 nM of each peptide was diluted in each medium and injected for in vitro experiments. The NPY $D^{25}$(21-28) refers to a peptide in which arginine, the fifth amino acid of the amino acid sequence of NPY (21-28), is modified to D-type, the NPY $D^{26}$(21-28) refers to a peptide in which the sixth amino acid histidine is modified to D-form, and the $D^{25,26}$(21-28) refers to a peptide in which both the fifth and sixth amino acids are modified to D-form, respectively.

To make an osteoporosis model, 10-18 12 weeks old female mice per group underwent ovarian ablation. A week later, 50 μg/kg of NPY(21-28), NPY $D^{25}$(21-28), NPY $D^{26}$(21-28), NPY $D^{25,26}$(21-28), Osteopep2, NPY and 100 μl of PBS(Gibco) were intraperitoneally administered twice a day for 4 weeks at 12 hour intervals. Alendronate (Sigma), used as a competitive drug, was intraperitoneally administered once a week for 4 weeks at a dose of 50 μg/kg. As a control group, only Sham model of osteoporosis was performed by subcutaneous dissection of female mouse. Mice were placed in experimental groups using the Block randomization method, and all mouse experiments were approved through the Kyungpook National University Institutional Animal Care and Use Committee.

1-2. Culture of Mesenchymal Stem Cells in Bone Marrow and Induction of Differentiation Into Osteoblasts Four to six weeks old C57BL/6 mice were sacrificed after anesthesia, and then tibias and femurs were dissected. Bone marrow was harvested from tibias and femurs and single cell suspensions were obtained using a 40 μm cell strainer (Becton-Dickinson LAβware, Franklin Lakes, N.J.). Approximately 107 cells were dispensed into 75-cm 2 flasks containing mesenchymal stem cells Stimulatory Supplements with antibiotics (Stem Cell Technologies, Inc) and MesenCult™ MSCBasal medium. The cells were incubated for 1 week and further incubated for 3 weeks with StemXVivo Osteogenic/Adipogenic Base Media (R & D systems) supplemented with StemXVivo Osteogenic supplement (20×) and penicillin-streptomycin (100×) for differentiation into osteoblasts.

The cultures were replaced every two to three days.

1-3. Real-Time Quantitative PCR

Real-time quantitative PCR was used to measure expression levels of hematopoietic stem cell adhesion factors (Sdf-1a, KitI, Angpt1) present in osteoblasts. Total RNA was extracted from cell eluate and bone marrow cells using the RNeasy Plus mini kit (Qiagen, Korea, Ltd), and cDNAs were synthesized from 5 μg total RNA using a kit in Clontech (Mountain View, Calif.). In addition, using a Corbett research RG-6000 real-time PCR instrument, Real-time quantitative PCR was performed at 95° C. for 10 minutes; at 95° C., for 10 seconds; at 58° C., for 15 seconds; at 72° C. for 20 seconds as one cycle, and 40 cycles were repeated. Primers used for the real-time quantitative PCR are shown in Table 1.

TABLE 1

| | | |
|---|---|---|
| SDF-1 α | F 5'-TTCCTATCAGAGCCCATAGAG-3' | SEQ ID NO: 9 |
| | R 5'-CCAGACCATCCTGGATAATG-3' | SEQ ID NO: 10 |
| Kit ligand (stem cell factor; SCF) | F 5'-CCAAAAGCAAAGCCAATTACAAG-3' | SEQ ID NO: 11 |
| | R 5'-AGACTCGGGCCTACAATGGA-3' | SEQ ID NO: 12 |
| Angiopoietin-1 (Angpt1) | F 5'-ACGGGGGTCAATTCTAAG-3' | SEQ ID NO: 13 |
| | R 5'-GCCATTCCTGACTCCACA-3' | SEQ ID NO: 14 |
| GAPDH | F 5'-TTGCTGTTGAAGTCGCAGGAG-3' | SEQ ID NO: 15 |
| | R 5'-TGTGTCCGTCGTGGATCTGA-3' | SEQ ID NO: 16 |

1-4. Colony-Forming Unit (CFU) Assays

CFU analysis was performed to determine the number of bone marrow hematopoietic progenitor cells in the blood of mice. After anesthetizing the mouse first, 500 μl to 700 μl of blood were collected in a heparin tube by cardiac drawing, and then placed in ammonium chloride solution (Stem Cell Technologies, Inc. 1:10) and placed on ice for 15 minutes to remove red blood cells. The red blood cells were well shaken at intervals of 2 to 3 minutes and centrifuged at 1000 rpm for 7 minutes. The supernatant was removed and washed with IMDM (Gibco) supplied with 2% fetal bovine serum (FBS, Gibco). The washed cells ($3\times10^5$ per mouse) were divided into three 35 mm dishes containing methylcellulose-based media (Methocult, Stem cell), and after the cells were incubated for two weeks, the number of colonies formed in the flask was counted.

1-5. Flow Cytometry Analysis (FACs)

To examine the changes in the number of myelopoiesis stem cells in the bone marrow of the mouse, the bone marrows of mice were collected and analyzed by FACs using five antibodies such as Lineage, Sca-1, c-kit, CD150, and CD48 as markers of myelopoiesis stem cells. For the analysis of myelopoiesis stem cell, bone marrow collected from the tibias and the femurs in the animal models of osteoporosis injected with each peptide was removed from red blood cells with ammonium chloride solution (Stem Cell Technologies, Inc. 1:4). After washing with PBS (Gibco) solution containing 10% fetal bovine serum (FBS, Gibco) and 1% sodium azide (Sigma-Aldrich), it was centrifuged at 300×g for 10 minutes. Hematopoietic cells contained in bone marrow were removed with MACs beads (Miltenyi Biotec) using biotinylated lineage antibody (Miltenyi Biotec). The remaining cells were reacted for 30 minutes at 4° C. using Sca-1-PECY7, c-kit-APC, CD150-PE, and CD48-FITC (BD science) antibodies, and then were analyzed by LSRII (BD science) flow cytometry.

1-6. Micro CT

The femurs were separated from the mouse and refrigerated in 80% ethanol, and in order to measure change of bone density, the bone volume/total volume and trabecular thickness were measured by analyzing the area between 0.7 mm and 2.3 mm from the growth plate baseline with the Quantum FX microCT Imaging System.

1-7. Immunohistochemistry

The femurs were separated from the mice and fixed in 4% paraformaldehyde for 24 hours, and tissue was decalcified in 10% EDTA for 5 weeks. It was then dehydrated with a series of diluted alcohols, paraffinized, and prepared into 5 mm paraffin sections.

For TRAP staining, sections were deparaffinized, stained with 1.33 mM Fast Red Violet LB Salt (Sigma-Aldrich) in 50 mM sodium acetate (pH 5.0) containing 225 µM Naphthol AS-MX phosphate (Sigma-Aldrich, St Louis, Mo., USA), 0.84% N, N-dimethylformamide (Sigma-Aldrich) and 50 mM sodium tartrate, and incubated for 30 minutes. After incubation, the sections were washed with distilled water and counterstained with 1% methyl green.

For H & E staining, the deparaffinized sections were stained with Harris hematoxyline for 8 minutes, washed with distilled water, and stained with Eosin for 1 minute.

Histomorphometric analysis was performed using the OsteoMeasure program (Extensive interactive Bone Histomorphometry Analysis System).

1-8. Statistical Analysis

Comparison with each group was performed by one way ANOVA and Tukey's HSD test. All statistical analyzes were performed using SPSS statistical software. It was considered significant for $p<0.05$.

Example 2 Effects of NPY (21-28), NPY (24-31), NPY (29-36) on the Expression of Myelopolesis Stem Cell Adhesion Factors in Osteoblasts To investigate the effect of NPY (21-28), NPY (24-31) and NPY (29-36), which are recombinant peptides consisting of eight amino acid sequences, on the expression of hematopoietic stem cell adhesion factors (Sdf-1a, KitI, Angpt1) present in osteoblasts, the following experiments were carried out according to the methods of Examples 1-1 and 1-2, 1-3.

First, bone marrow was harvested from 4 to 6 weeks old C57BL6 mice, and mesenchymal stem cells (BM-MSCs) in bone marrow were collected, and then cultured for 3 weeks in osteoblast differentiation induction medium for the differentiation into osteoblasts. After 28 days, each peptide was treated with 10 nM for 3 days, and bone cells were collected and examined for expression levels of three adhesion factors by real-time quantitative PCR. Osteopep2 and its parent NPY were used as positive controls.

The schematic diagram of the experimental procedure and the result of measuring the expression amount of the adhesion factor are shown in FIGS. 1A to 1D.

As shown in FIGS. 1A to 1D, when compared to osteoblasts (control) not treated with peptides, the expression levels of Sdf-1a, KitI, and Angpt1 were decreased only in osteoblasts treated with NPY (21-28) among NPY (21-28), NPY (24-31), and NPY (29-36) peptides ($p<0.05$, n=3 per group). From these results, it was found that only NPY (21-28) of the three peptides recombined with eight amino acids decreased the expression levels of myelopoiesis stem cell adhesion factors present in osteoblasts, which may induce the release of myelopoiesis stem cell from bone marrow to blood. In other words, NPY (21-28) was found to be a peptide comprising an active site capable of inducing the release of myelopoiesis stem cell into blood.

Figure 2A:
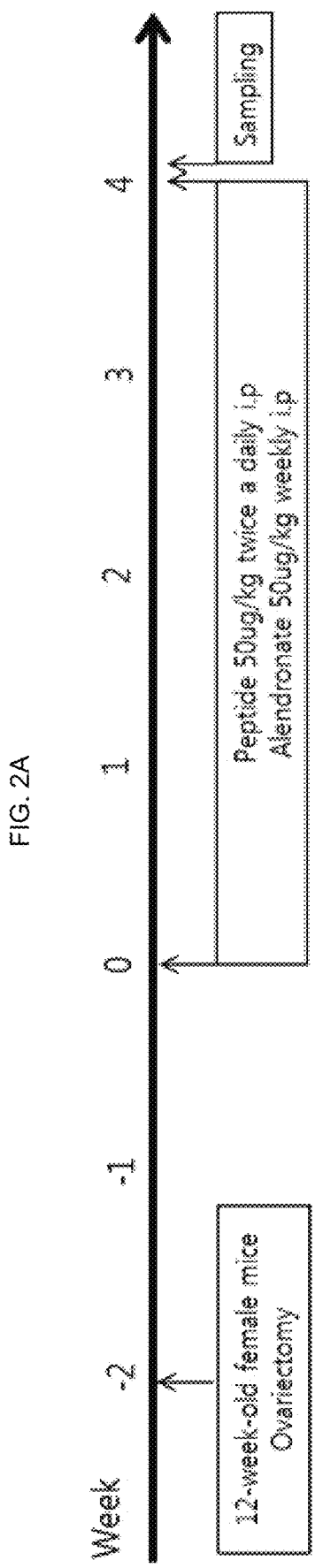
FIG. 2A is a summary of the experiment performed to determine the effect of NPY (21-28) on the osteoporosis relief through releasing of myelopoiesis stem cells into blood.

Example 3. Effect of NPY (21-28) of the Present Invention on Releasing Myelopolesis Stem Cells into Blood in Animal Models of Osteoporosis In order to investigate whether the NPY (21-28) of the present invention affects the blood release of myelopoiesis stem cells in the animal models of osteoporosis, the following experiments were carried out according to the methods of Examples 1-1, 1-3, 1-4, and 1-5. In order to make animal models of osteoporosis, 12 weeks old C57BL/6 female mice were subjected to ovarian ablation for 10 to 18 animals in each group. One week later, 50 µg/kg of NPY (21-28) and 100 µl of PBS (Gibco) were intraperitoneally administered twice a day for 4 weeks at 12 hour intervals. As a control group, mice that underwent only subcutaneous incisions in normal mice were used. Weight change was measured weekly, and bone marrow and blood were collected one hour after the last dose at 4 weeks, and the release of myelopoiesis progenitor and stem cells into blood was analyzed. The positive control group, NPY (21-36), Osteopep2 and full length NPY (50 µg/kg, intraperitoneally administered twice a day for 4 weeks) were used. Alendronate used as a competitive drug for osteoporosis treatment was intraperitoneally administered at a dose of 50 µg/kg for 4 weeks once a week. The schematic diagram of an experimental procedure is shown in FIG. 2A.

Figure 2B:
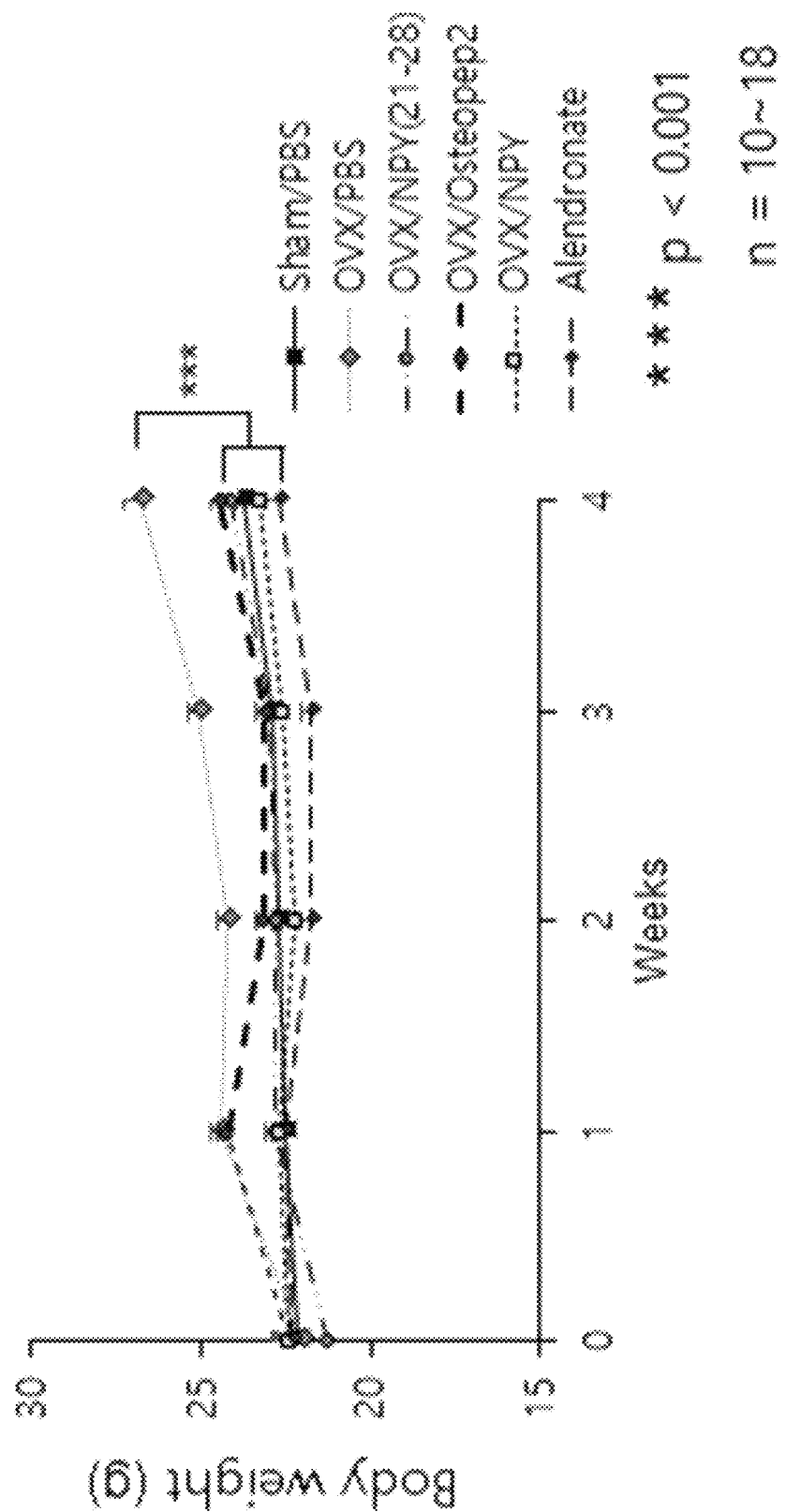
FIG. 2B is the result showing the weight change after administration of each peptide to the animal models of osteoporosis (Sham: control animal models with subcutaneous incision only, OVX: osteoporosis animal models with ovarian resection after subcutaneous incision).

3-1. Effect of NPY (21-28) on Weight Gain by Osteoporosis in Animal Models of Osteoporosis In order to investigate the effect of NPY (21-28) of the present invention on weight gain induced by osteoporosis, body weight was measured once a week for a total of 4 weeks of NPY (21-28) injection. The results are shown in FIG. 2B. As shown in FIG. 2B, the group injected with PBS in the animal models of osteoporosis gained weight according to time, while the group injected with NPY (21-28) did not change in weight ($p<0.05$, n=10-18 per group). From the above results, it can be seen that NPY (21-28) can suppress the weight gain caused by osteoporosis.

3-2. Effect of NPY (21-28) on the Expression of Myeloid Stem Cell Adhesion Factors in Animal Models of Osteoporosis To investigate the effect of NPY (21-28) of the present invention on the expression level of adhesion factor involved in the maintenance of myelopoiesis stem cells in bone marrow of the animal models of osteoporosis, bone marrow was harvested from tibias and femurs of mice 1 hour after the last administration of NPY (21-28) at 4 weeks. The expression levels of the adhesion factors were examined by real-time quantitative PCR, which is the method described in the Example 1-3.

Figure 3C:
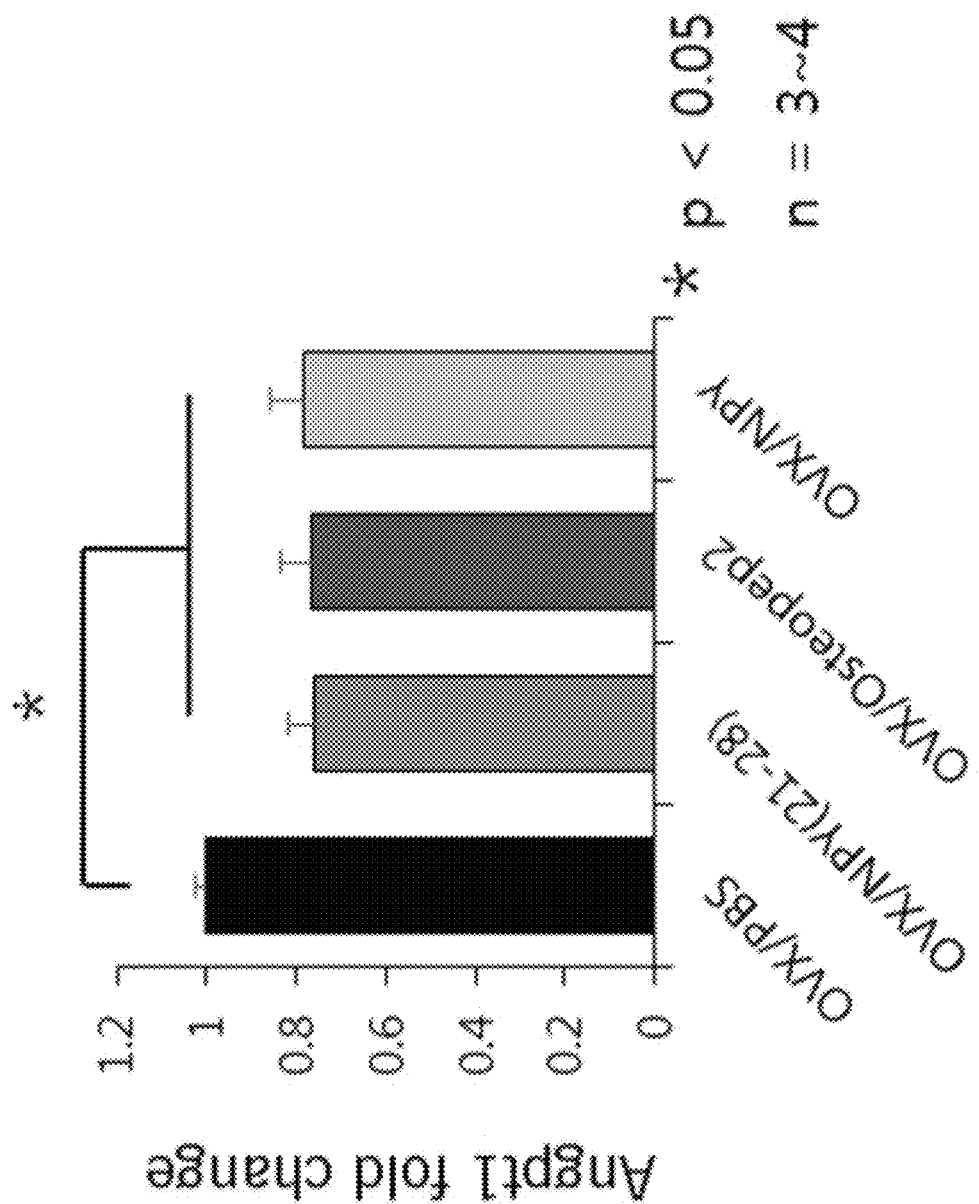

The results are shown in FIGS. 3A to 3C. As shown in FIGS. 3A to 3C, expression levels of major adhesion factors of Sdf-1a, KitI, and Angpt1 were decreased ($p<0.05$, $n=3-4$ per group).

3-3. Effect of NPY (21-28) on Releasing Myelopolesis Progenitor Cells and Myelopoiesis Stem Cells into Blood in Animal Models of Osteoporosis To investigate the effect of NPY (21-28) of the present invention on myelopoiesis progenitor cells and myelopoiesis stem cells released into the blood in osteoporosis animal model, it was confirmed through the CFU assay and FACs, which are the methods described in Examples 1-4 and 1-5.

Figure 4B:
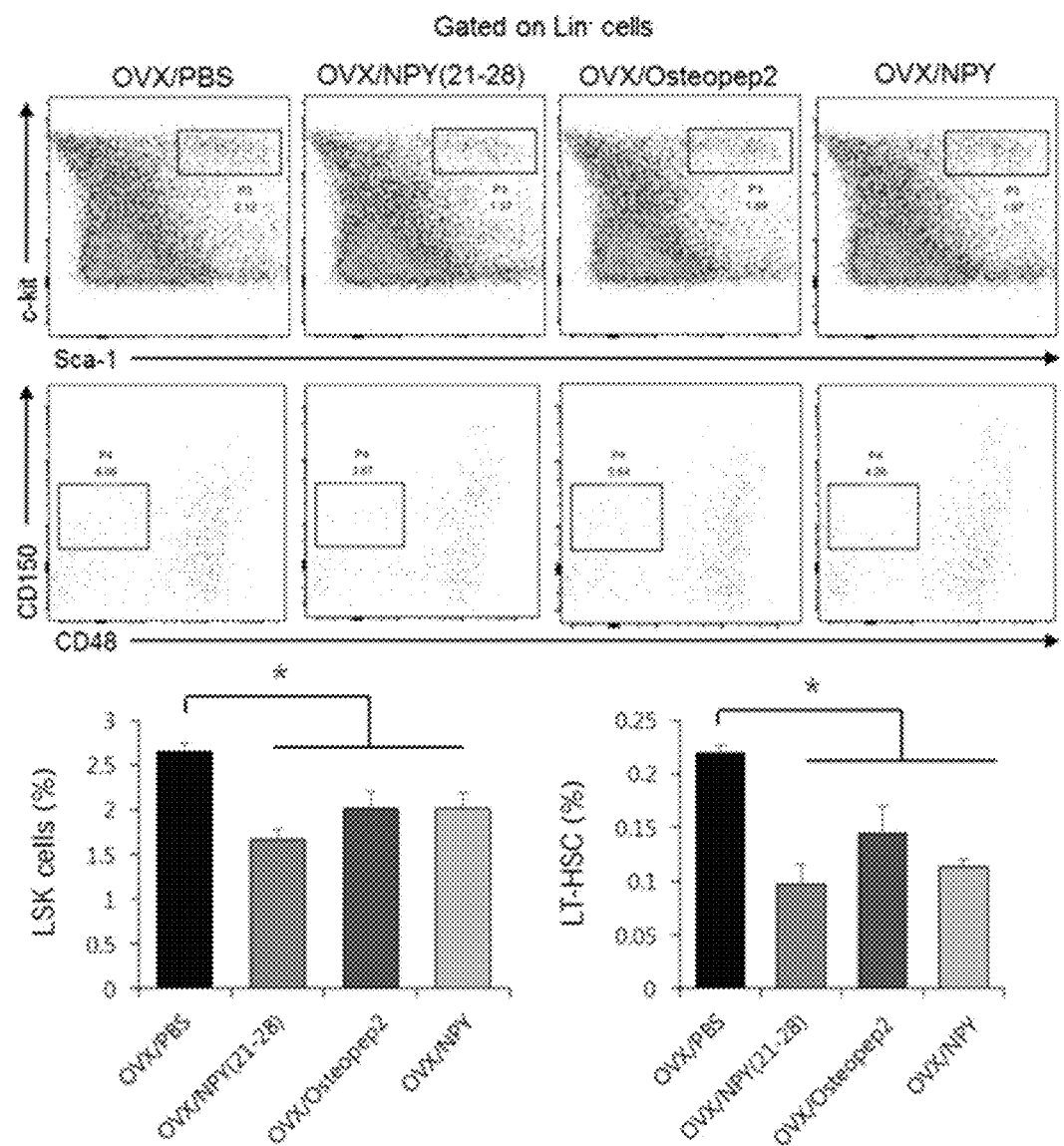
FIG. 4B is a graph showing the number of hematopoietic stem cells in the bone marrow using a marker of myelopoiesis stem cells and quantifying them (OVX: osteoporosis animal models with ovarian resection after subcutaneous incision).

The results are shown in FIGS. 4A and 4B. As shown in FIGS. 4A and 4B, (a) CFU assay showed that NPY (21-28) increases releasing myelopoiesis progenitor cells into blood in the animal model of osteoporosis ($p<0.05$, $n=4-5$ per group). As a result, it was confirmed through the FACs that (b) the number of myelopoiesis stem cells remaining in the bone marrow was reduced ($p<0.05$, $n=4-5$ per group).

From the above results, the administration of NPY (21-28) of the present invention can induce releasing myelopoiesis progenitors and its stem cells into blood by reducing the expression levels of adhesion factors of myelopoiesis stem cells present in osteoblasts. The effect of NPY (21-28) was confirmed to be superior to Osteopep2 and NPY used as a positive control.

Example 4. Effect of NPY (21-28) of the Present Invention on the Prevention and Treatment of Osteoporosis In order to investigate whether releasing myelopoiesis stem cells into blood by administration of NPY (21-28) of the present invention has the effect of alleviating a decrease of bone density of osteoporosis, the following experiments were carried out according to the methods of Examples 1-6 and 1-7.

4-1. Changes in Bone Density by NPY (21-28) Administration in Animal Models of Osteoporosis Femurs were separated from mice after the last administration of NPY (21-28) at 4 weeks. To determine the change of bone density, bone density (bone volume/total volume) and bone tissue thickness (trabecular thickness) were measured with the Quantum FX microCT Imaging System.

Figure 5A:
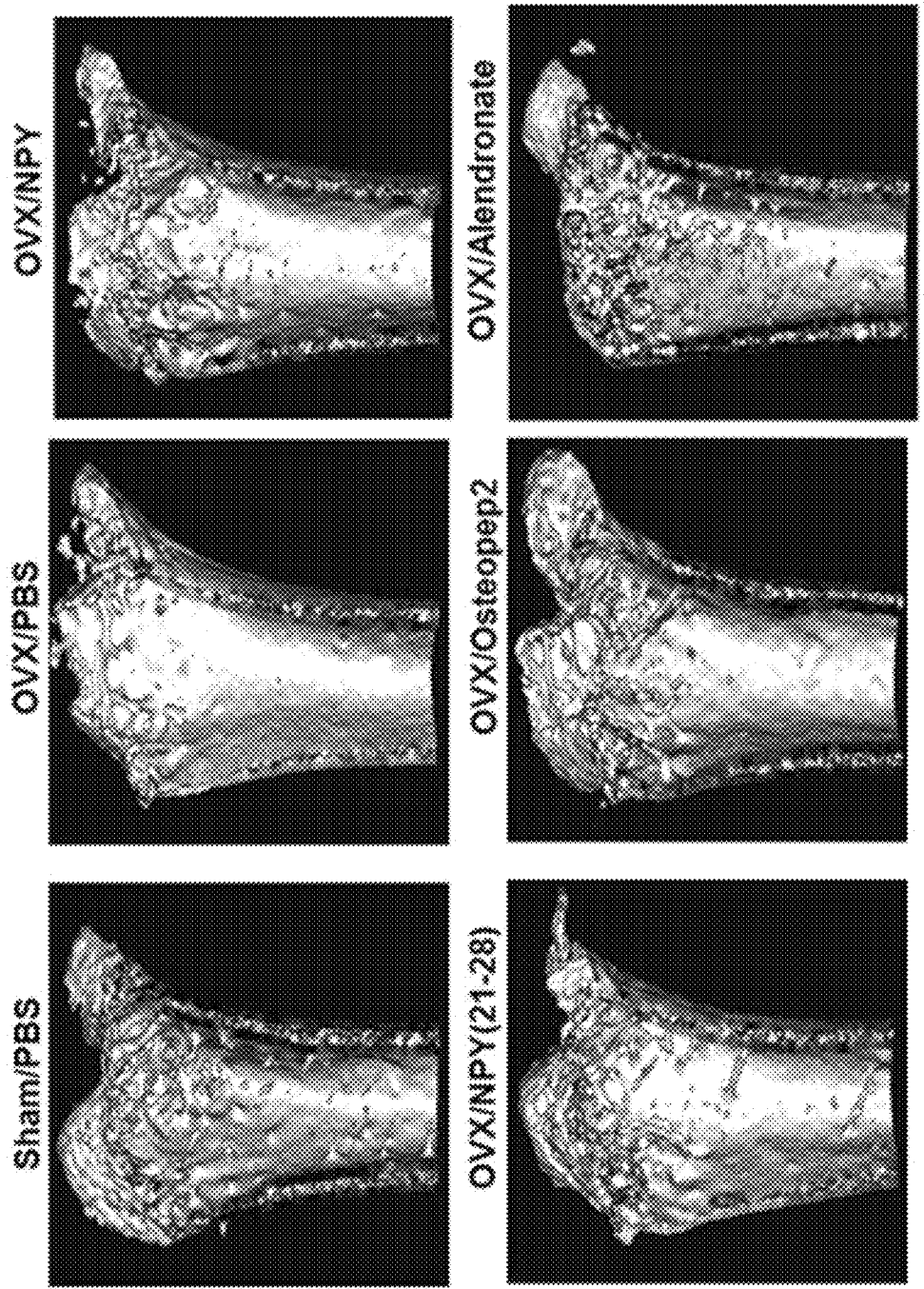

The results are shown in FIGS. 5A to 5C. As shown in FIGS. 5A to 5C, the microCT photographs showed that the percentage of bone density (BV/TV, %) and bone tissue thickness (trabecular thickness, mm) of the mice injecting NPY in the animal models of osteoporosis were increased compared to the mice injected with PBS. In addition, the effect of NPY (21-28) was better than that of the Osteopep2 and NPY as positive control group. It showed similar effects as the mice injected with the competitive drug Alendronate ($p<0.05$, $n=4-5$ per group).

4-2. Osteoclast Changes in Bone Marrow by NPY (21-28) Administration in Animal Models of Osteoporosis After the last administration at 4 weeks of NPY (21-28), the femurs were separated from the mice and the number of osteoclasts in the bone marrow was measured by TRAP staining.

Figure 6A:
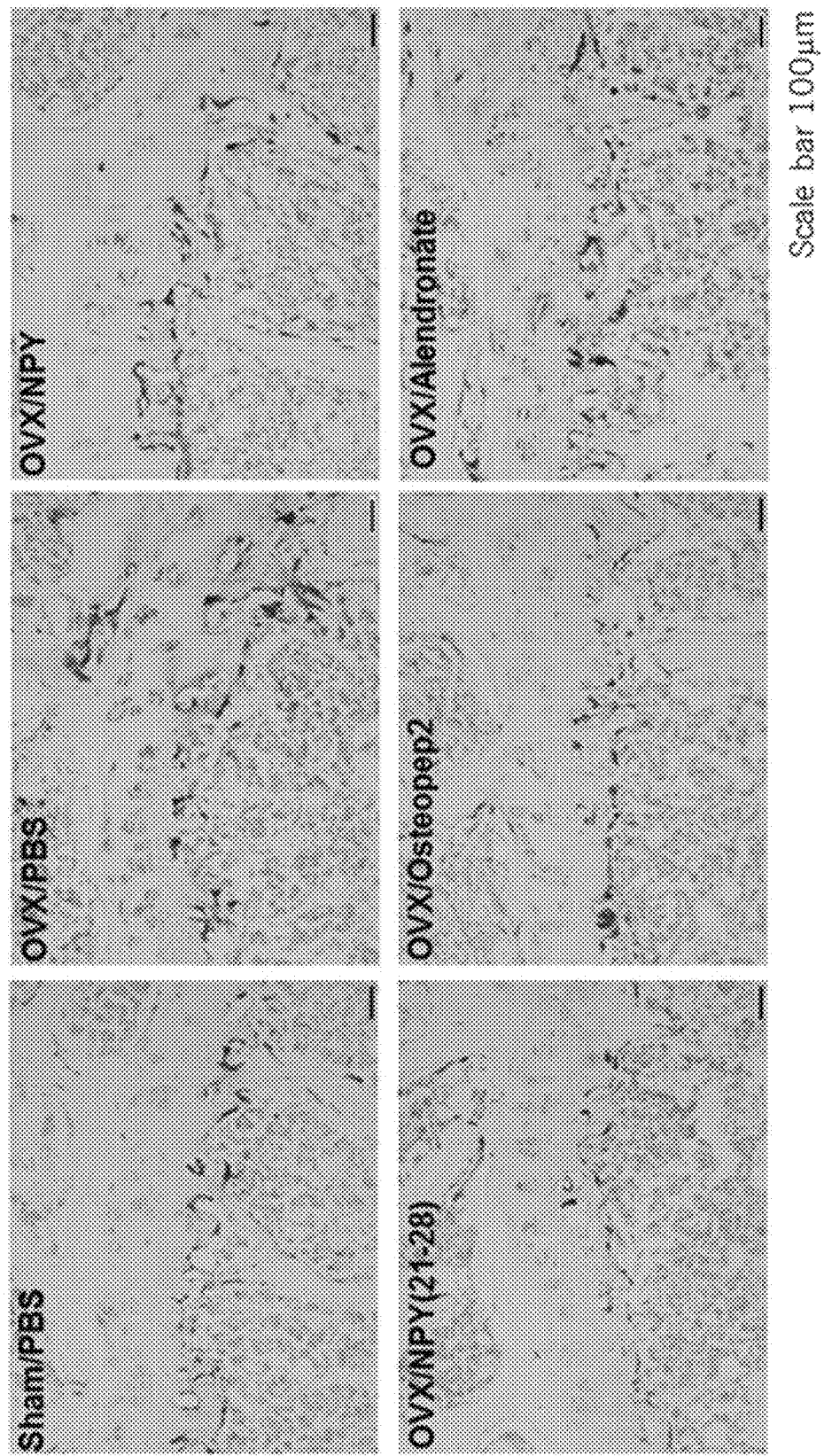
Figure 6B:
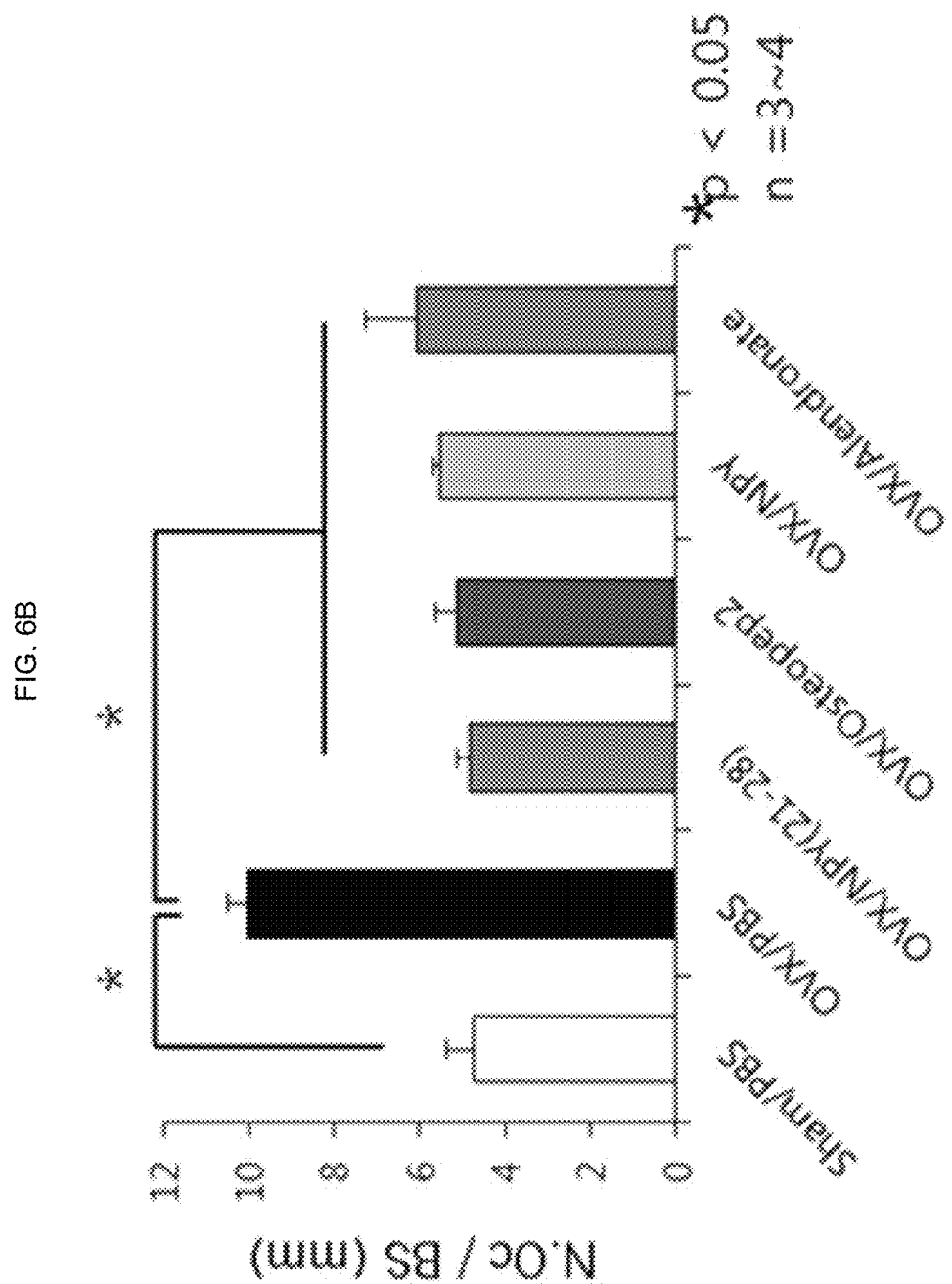

The results are shown in FIGS. 6A to 6C. As shown in FIGS. 6A to 6C, the number of TRAP positive osteoclasts in bone marrow of mice injecting NPY (Number of osteoclast/Bone surface, mm) and the osteoclast surface (Osteoclast surface/Bone surface, %) were reduced compared to mice injected with PBS ($p<0.05$, $n=3-4$ per group). In addition, the effect of NPY (21-28) was not only superior to Osteopep2 and NPY as the positive control group, but it was also found to be superior to the competitive drug Alendronate.

4-3. Changes of Osteoblast in Bone Marrow by NPY (21-28) Administration in Animal Models of Osteoporosis After the last administration of 4 weeks of NPY (21-28), the femurs were separated from the mice, and the number of osteoblasts in bone marrow was measured by H & E staining.

Figure 7C:
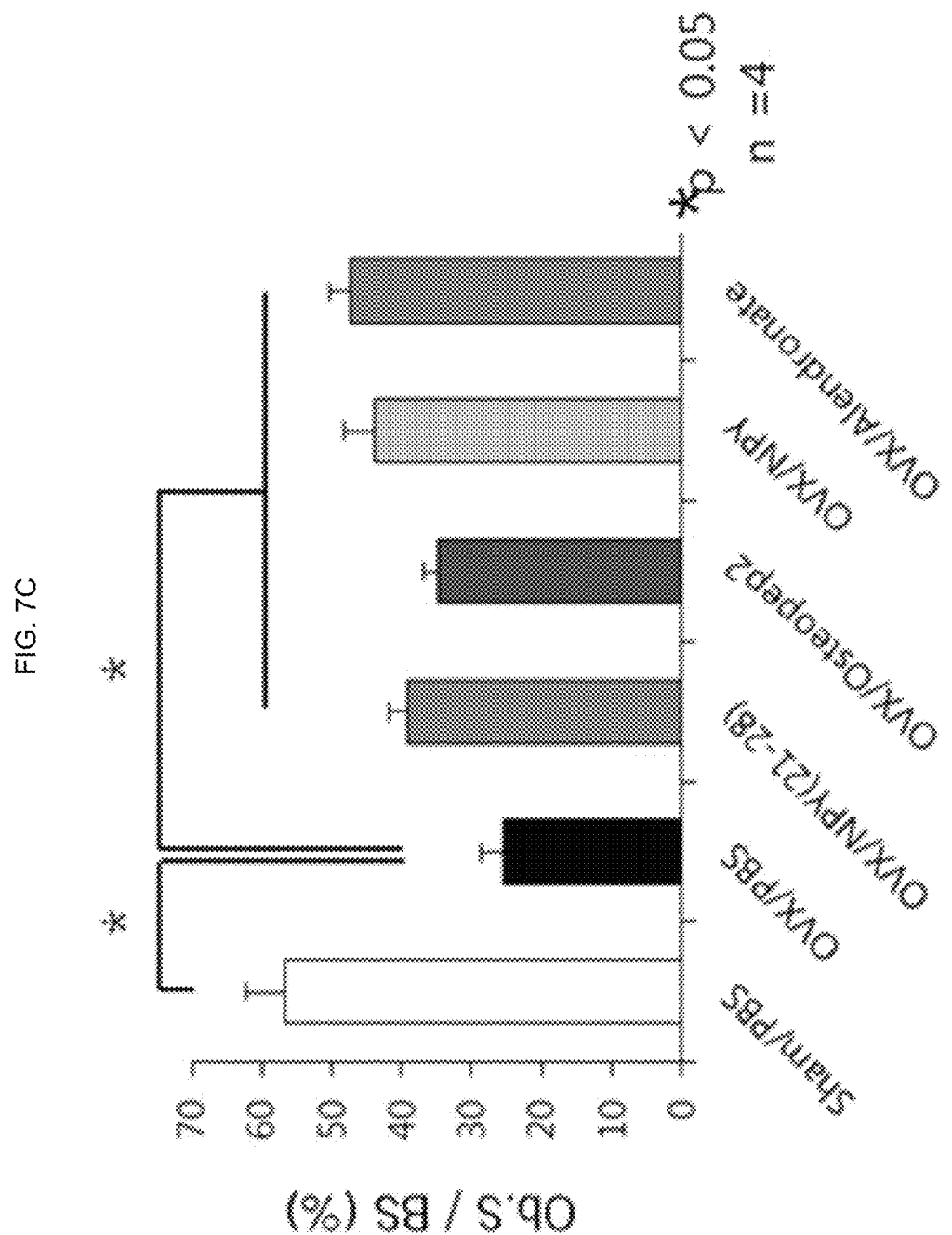
Figure 8A:
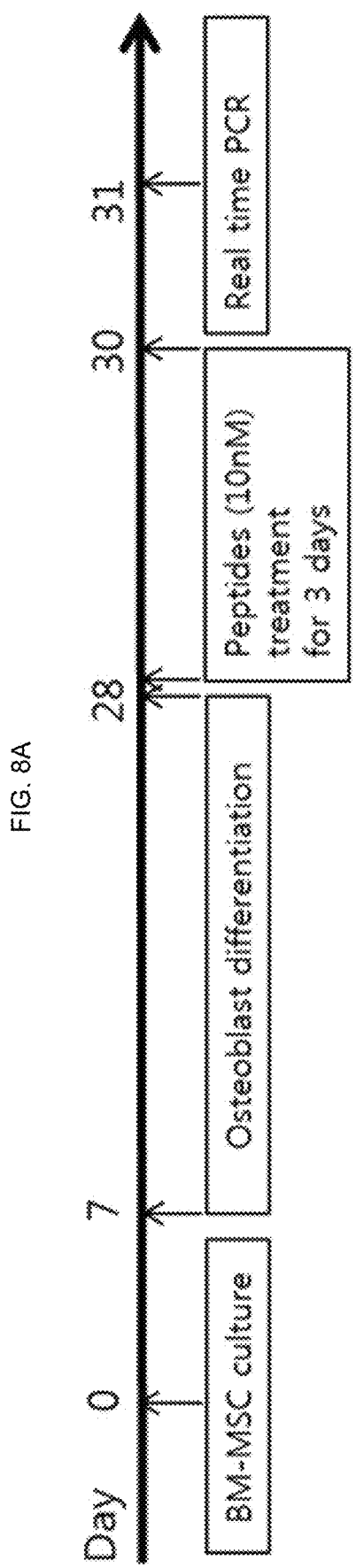
FIGS. 8A to 8D are a result showing the change in the expression levels of the adhesion factors after treating the three kinds of peptides, NPY $D^{25}$(21-28), NPY $D^{26}$(21-28), and NPY $D^{25,26}$(21-28) recombined by modifying the structure of specific amino acids to increase the receptor affinity of NPY (21-28) to osteoblasts that express adhesion factors of myelopoiesis stem cells (8A: summary of the experiment, 8B to 8D: a graph showing the expression levels of adhesion factors with fold change relative to the control group).
Figure 8B:
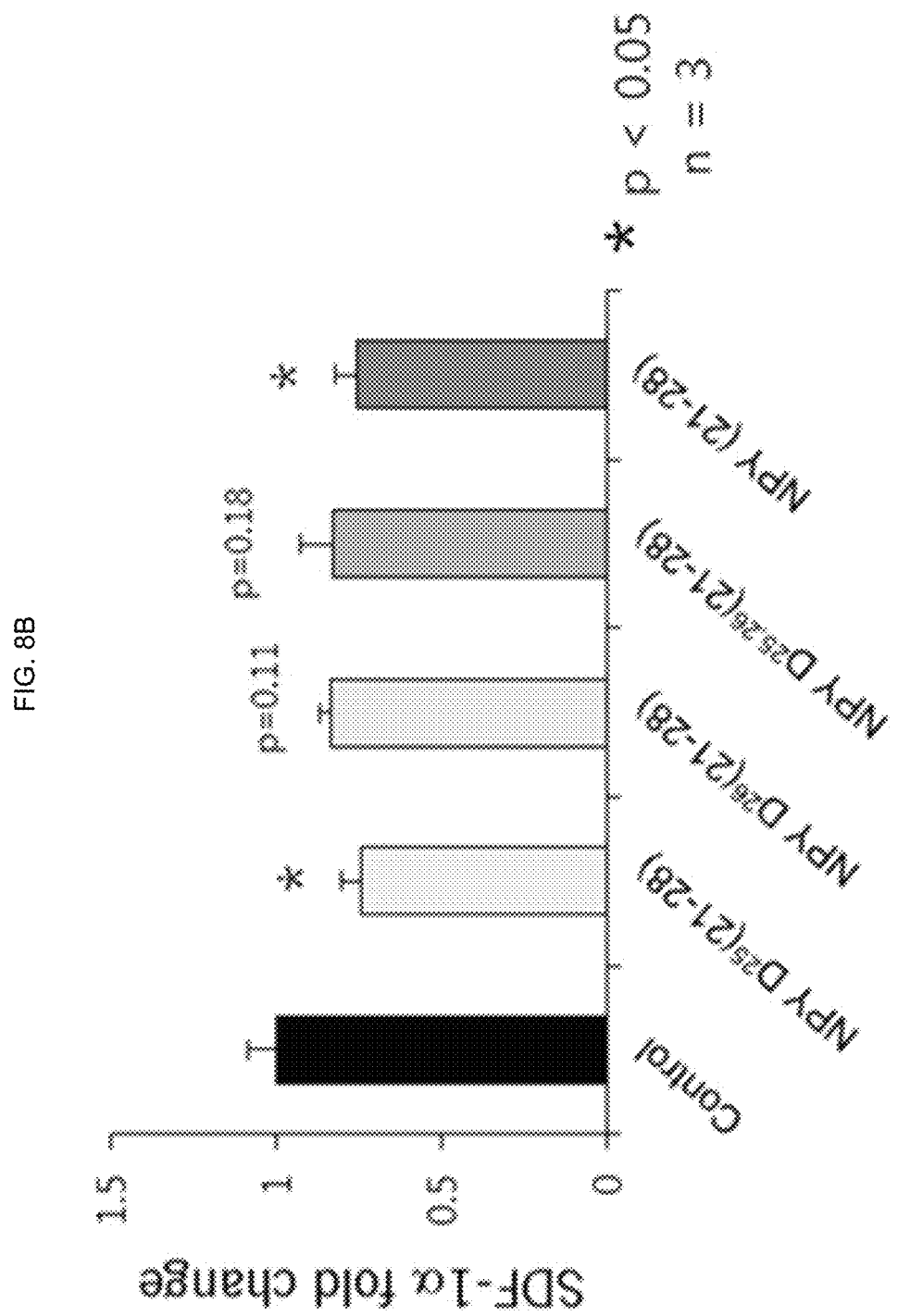
Figure 8C:
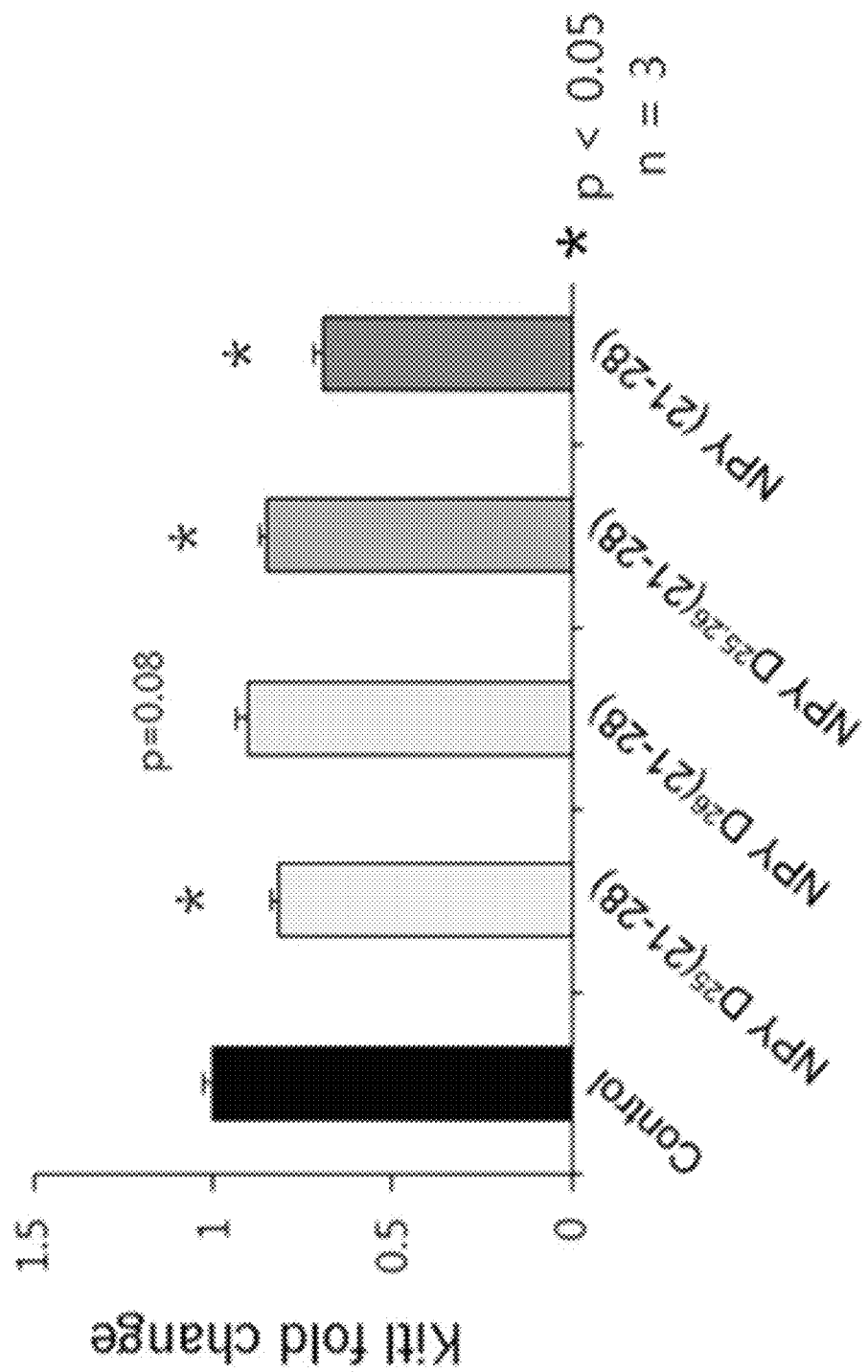
Figure 8D:
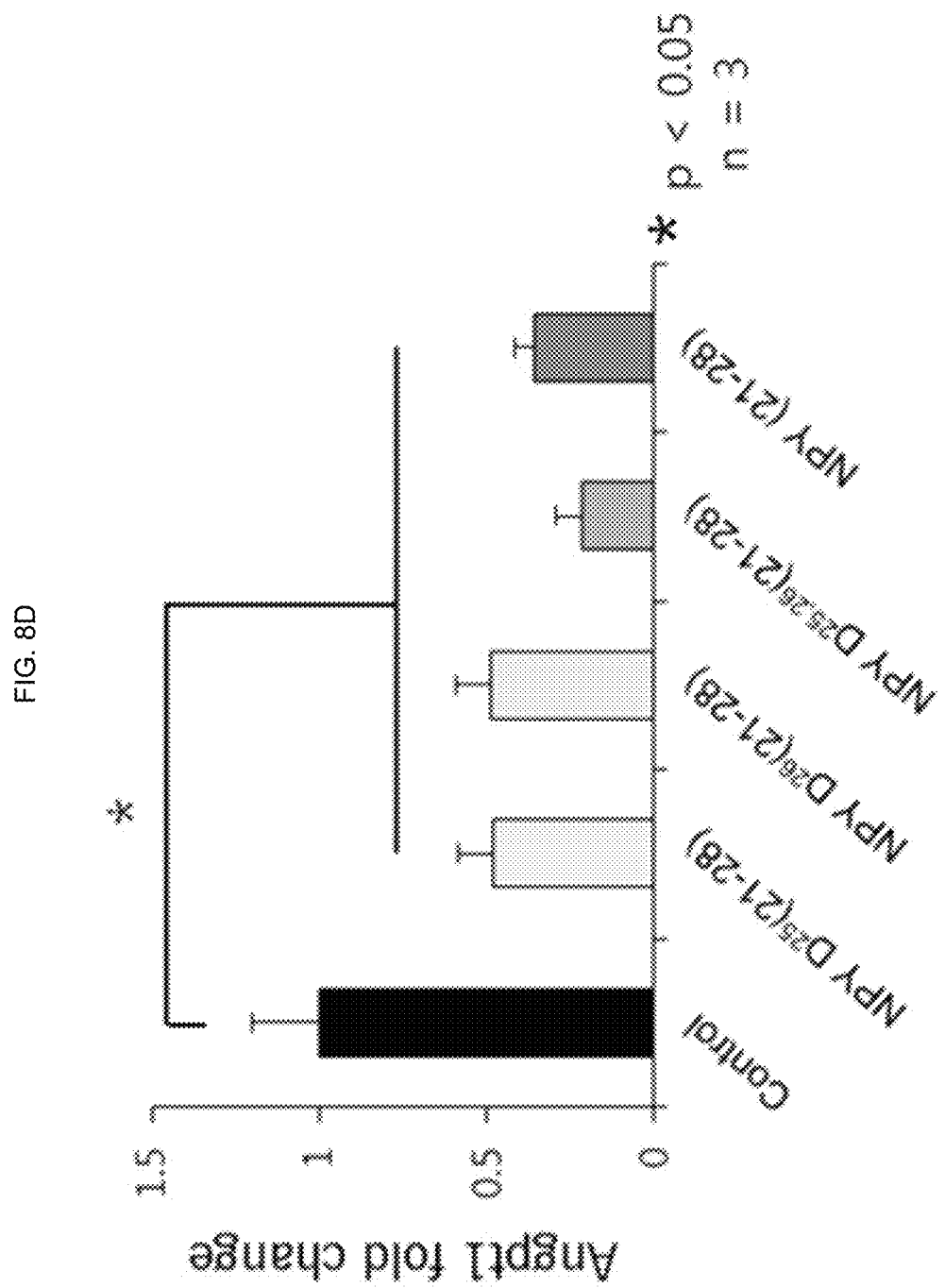

The results are shown in FIGS. 7A to 7C. As shown in FIGS. 7A to 7C, the number of osteoblast (Number of osteoblast/Bone surface, mm) and the osteoblast surface (Osteoblast surface/Bone surface, %) adjacent to the bone in the bone marrow of the mice to which NPY (21-28) was administered were increased compared to mice injected with PBS, and this effect was better than that of Osteopep2 as the positive control group ($p<0.05$, $n=4$ per group).

From these results, it was found that NPY (21-28) inhibits the reduction in bone density and bone tissue thickness of osteoporosis mice by reducing the number of osteoclasts that differentiate from hematopoietic stem cells in the bone marrow and by simultaneously increasing the number of osteoblasts after inducing the release of myelopoiesis stem cells into blood in animal models of osteoporosis. In addition, NPY (21-28) is a short sequence peptide comprising the active site of Osteopep2 and/or NPY used as a positive control and showed a better effect than these. Thus, NPY (21-28) was found that it has an effect of preventing and treating osteoporosis.

Example 5. Effects of NPY $D^{25}$(21-28), NPY $D^{26}$ (21-28), NPY $D^{25,26}$(21-28)), in which the Structure of Specific Amino Acids were Modified to Increase Receptor Affinity of NPY (21-28) on the Expression of Myelopolesis Stem Cell Adhesion Factors in Osteoblasts To investigate effects of NPY $D^{25}$(21-28), NPY $D^{26}$(21-28), NPY $D^{25,26}$(21-28)), in which the structure of specific amino acids were modified to increase receptor affinity of NPY (21-28) on the expression of myelopoiesis stem cell adhesion factors (Sdf-1a, KitI, Angpt1) in osteoblasts, the following experiments were carried out according to the methods of Examples 1-1 and 1-2, 1-3.

The schematic diagram of the experimental procedure and the result of measuring the expression amount of the adhesion factors are shown in FIGS. 8A to 8D. As shown in FIGS. 8a to 8d, it was confirmed that the expression levels of Sdf-1a, KitI, and Angpt1 decreased in osteoblasts treated with NPY $D^{25}$(21-28), NPY $D^{26}$(21-28), and NPY $D^{25,26}$ (21-28), compared to the osteoblasts (control) not treated with peptides. In particular, NPY $D^{25,26}$ (21-28) was confirmed to further reduce the amount of Angpt1 expression than NPY (21-28).

From the above results, it was found that NPY $D^{25}$(21-28), NPY $D^{25}$(21-28), and NPY $D^{25,26}$(21-28) peptides which transformed the structure of a specific amino acid into D-form decreased the expression level of myelopoiesis stem cell adhesion factor present in osteoblasts, which may induce releasing of myelopoiesis stem cell from bone marrow into blood.

Example 6. Effects of NPY $D^{25}$(21-28), NPY $D^{26}$(21-28), NPY $D^{25,26}$(21-28) on Releasing Myelopolesis Stem Cells into Blood in Animal Models of Osteoporosis In order to investigate whether the NPY $D^{25}$(21-28), NPY $D^{26}$(21-28), and NPY $D^{25,26}$(21-28) affects releasing myelopoiesis stem cells into blood in the animal models of osteoporosis, the following experiments were carried out according to the methods of Examples 1-1, 1-3, 1-4, and 1-5.

6-1. Effects of NPY $D^{25}$(21-28), NPY $D^{26}$(21-28), and NPY $D^{25,26}$(21-28) on Weight Gain by Osteoporosis in Animal Models of Osteoporosis In order to investigate the effects of NPY $D^{25}$(21-28), NPY $D^{26}$(21-28), and NPY $D^{25,26}$(21-28) of the present invention on weight gain induced by osteoporosis, body weight was measured once a week for a total of 4 weeks in which each peptide was injected.

Figure 9A:
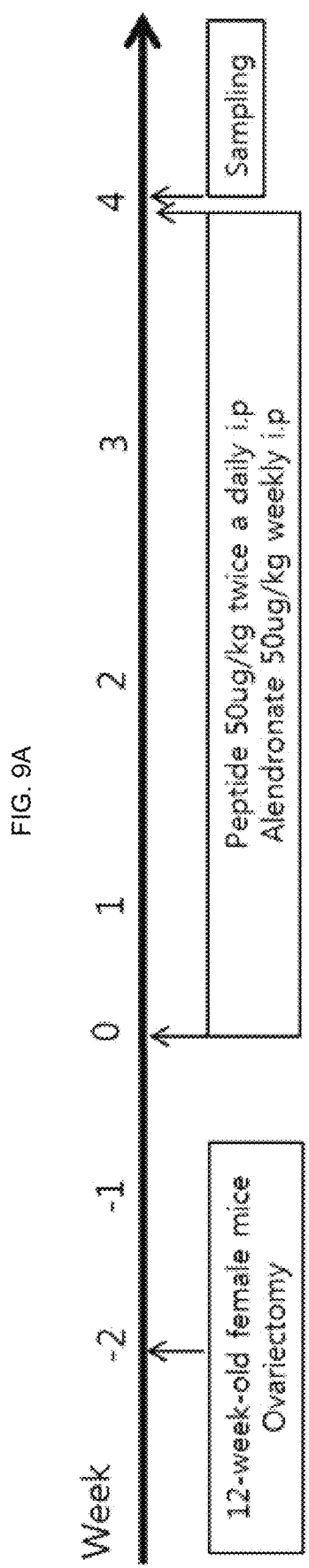
FIG. 9A is a summary of the experiment performed to determine the effect of NPY $D^{25}$(21-28), NPY $D^{26}$(21-28), and NPY $D^{25,26}$(21-28) on the osteoporosis relief through releasing myelopoiesis stem cells into blood.
Figure 9B:
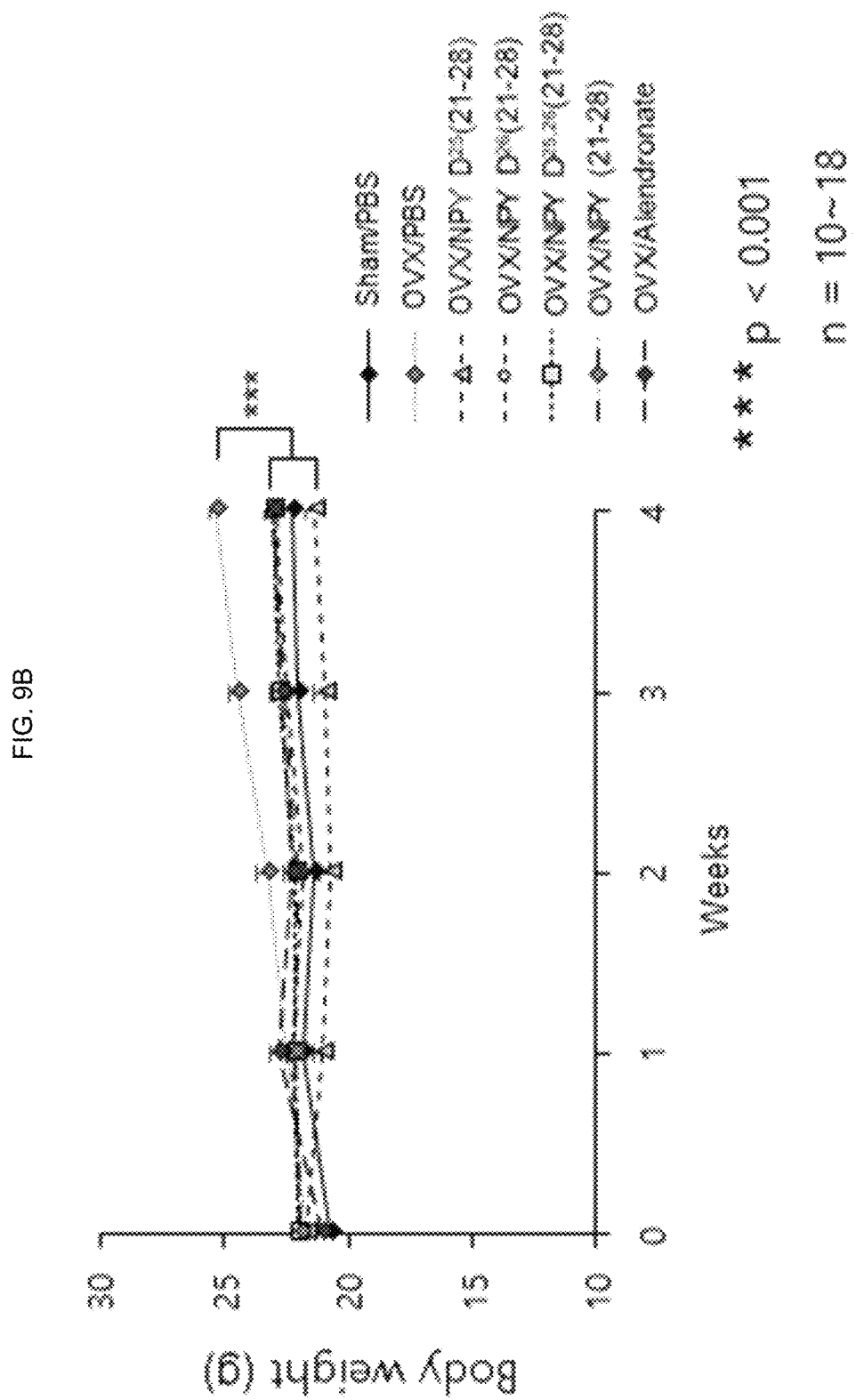
FIG. 9B is the result showing the weight change after administration of each peptide to the animal models of osteoporosis (Sham: control animal model with subcutaneous incision only, OVX: osteoporosis animal models with ovarian resection after subcutaneous incision).

The results are shown in FIGS. 9A and 9B. As shown in FIGS. 9A and 9B, the group injected with PBS in the animal models of osteoporosis gained weight according to time, while the group injected with NPY $D^{25}$(21-28), NPY $D^{26}$(21-28), and NPY $D^{25,26}$(21-28) did not change in weight (p<0.05, n=10-18 per group). From the above results, it can be seen that NPY $D^{25}$(21-28), NPY $D^{26}$(21-28), and NPY $D^{25,26}$(21-28) can suppress the weight gain caused by osteoporosis.

6-2. Effects of NPY $D^{25}$(21-28), NPY $D^{26}$(21-28), and NPY $D^{25,26}$(21-28) on the Expression of Myeloid Stem Cell Adhesion Factors in Animal Models of Osteoporosis To investigate the effect of NPY $D^{25}$(21-28), NPY $D^{26}$(21-28), and NPY $D^{25,26}$(21-28) of the present invention on the expression level of adhesion factor involved in the maintenance of myelopoiesis stem cells in bone marrow of the animal models of osteoporosis, bone marrow was harvested from tibias and femurs of mice 1 hour after the last administration of each peptide at 4 weeks. The expression levels of the adhesion factors were examined by real-time quantitative PCR, which is the method described in the Example 1-3.

Figure 10B:
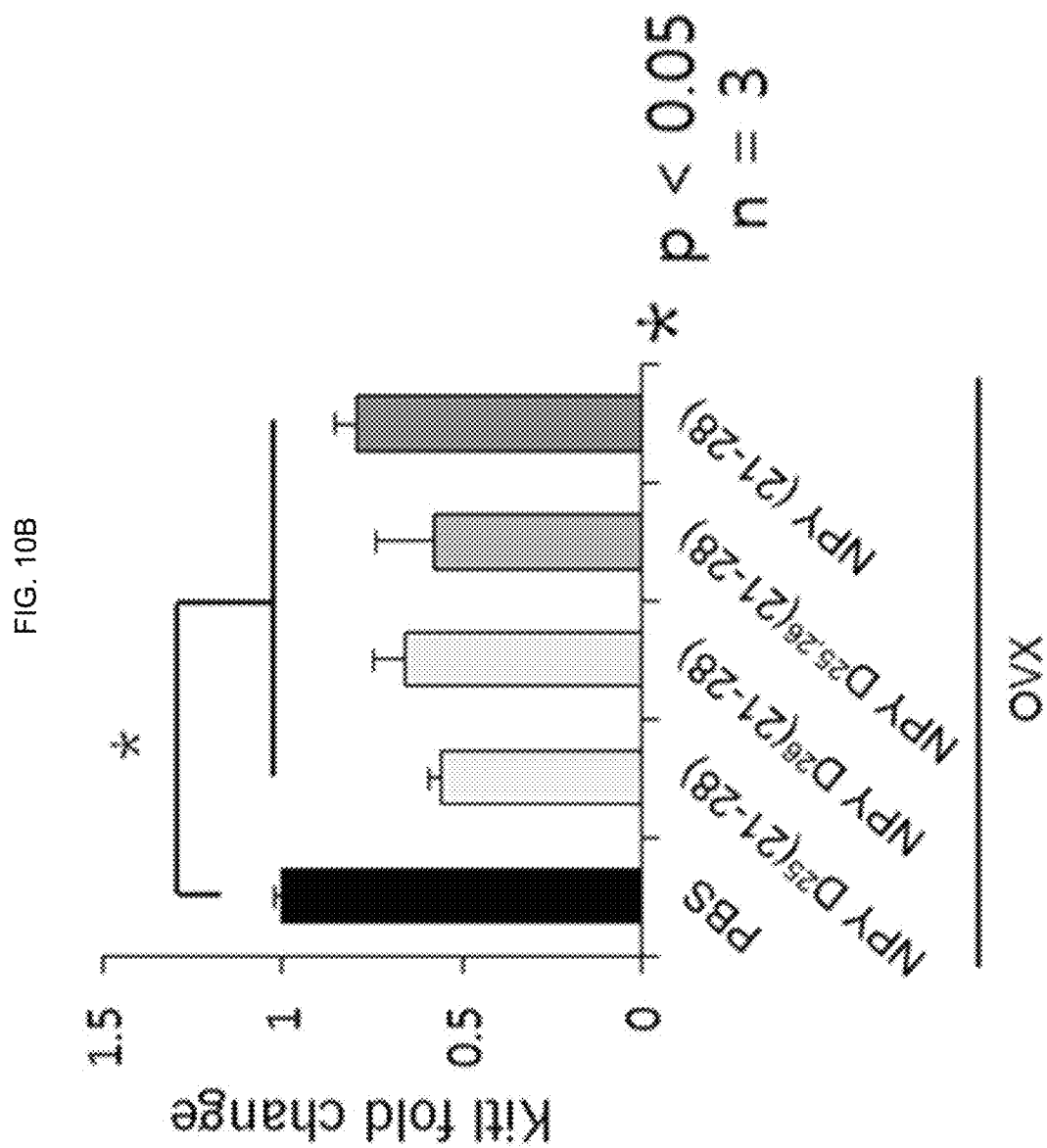

The results are shown in FIGS. 10A to 10C. As shown in FIGS. 10A to 10C, expression levels of major adhesion factors of Sdf-1a, KitI, and Angpt1 were decreased, and the effects were generally superior to those of NPY (p<0.05, n=3 per group).

6-3. Effects of NPY $D^{25}$(21-28), NPY $D^{26}$(21-28), and NPY $D^{25,26}$(21-28) on Releasing Myelopolesis Progenitor Cells and Myelopolesis Stem Cells into Blood in Animal Models of Osteoporosis To investigate the effect of NPY $D^{25}$(21-28), NPY $D^{26}$(21-28), and NPY $D^{25,26}$(21-28) on myelopoiesis progenitor cells and its stem cells released into the blood in osteoporosis animal model, it was confirmed through the CFU assay and FACs which are the methods described in Examples 1-4 and 1-5.

Figure 11A:
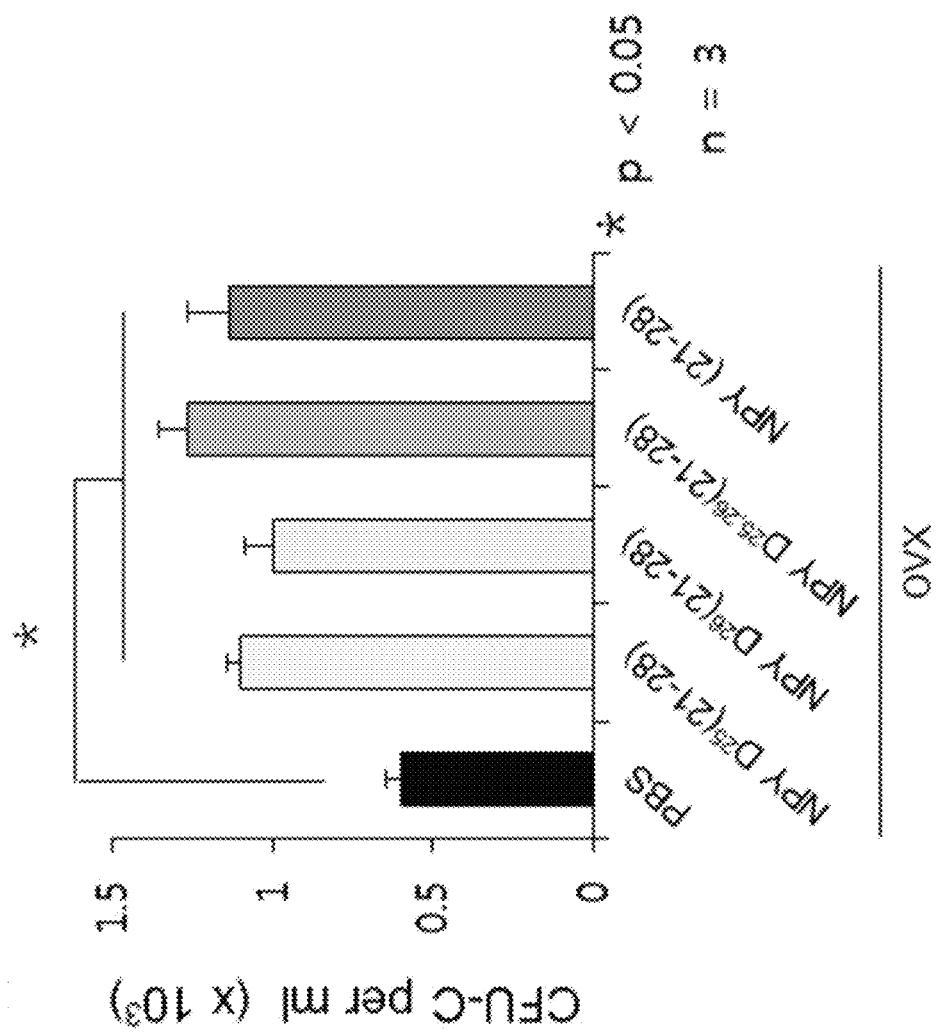
FIG. 11A shows the number of myelopoiesis progenitor cells in the blood after administration of each peptide in the animal models of osteoporosis.
Figure 11B:
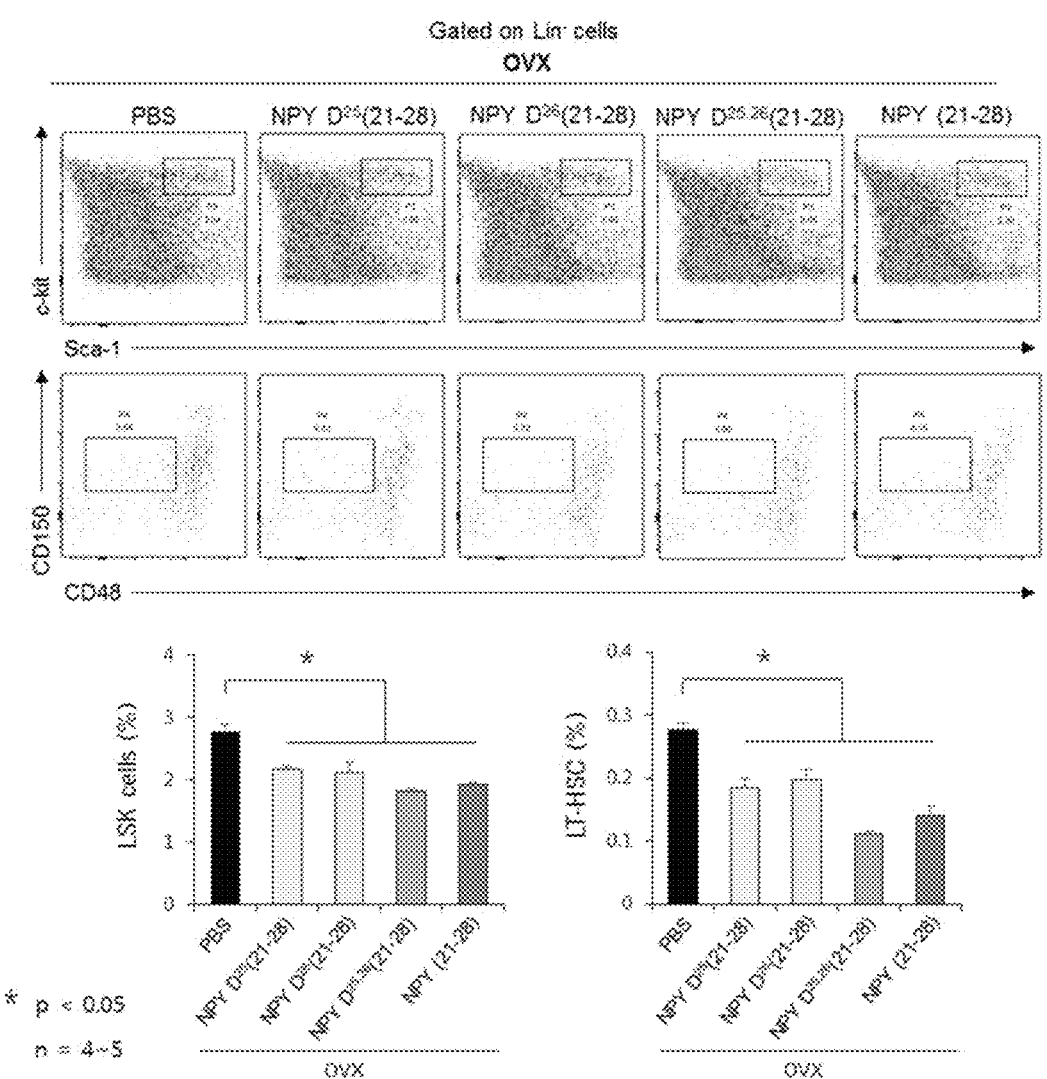
FIG. 11B is a graph showing the number of hematopoietic stem cells in the bone marrow using a marker of myelopoiesis stem cells and quantifying them (OVX: osteoporosis animal model with ovarian resection after subcutaneous incision).

The results are shown in FIGS. 11A and 11B. As shown in FIGS. 11A and 11B, (a) CFU assay showed that NPY $D^{25}$(21-28), NPY $D^{26}$(21-28), and NPY $D^{25,26}$(21-28) increases releasing myelopoiesis progenitor cells into blood in the animal model of osteoporosis (p<0.05, n=3 per group). As a result, it was confirmed through the FACs that (b) the number of myelopoiesis stem cells remaining in the bone marrow was reduced (p<0.05, n=4-5 per group). On the other hand, the effects of these D-type peptides were confirmed to be superior to those of NPY (21-28).

From the above results, the administration of NPY $D^{25}$(21-28), NPY $D^{26}$(21-28), and NPY $D^{25,26}$(21-28) of the present invention can induce releasing myelopoiesis progenitors and its stem cells into blood by reducing the expression levels of adhesion factors of myelopoiesis stem cells present in osteoblasts. In particular, among these peptides, NPY $D^{25,26}$ (21-28) was found to induce releasing myelopoiesis stem cells into blood with the highest efficiency, and the effect was even better than that of NPY (21-28).

Example 7. Effects of NPY $D^{25}$(21-28), NPY $D^{26}$(21-28), and NPY $D^{25,26}$(21-28) on Preventing and Treating Osteoporosis In order to investigate whether releasing myelopoiesis stem cells into blood by administration of NPY (21-28) has the effect of alleviating a decrease of bone density of osteoporosis, the following experiments were carried out according to the methods of Examples 1-6 and 1-7.

7-1. Changes in Bone Density by NPY $D^{25}$(21-28), NPY $D^{26}$(21-28), and NPY $D^{25,26}$(21-28) Administration in Animal Models of Osteoporosis Femurs were separated from mice after the last administration of NPY $D^{25}$(21-28), NPY $D^{26}$(21-28), and NPY $D^{25,26}$(21-28) at 4 weeks. To determine the change of bone density, bone density (bone volume/total volume) and bone tissue thickness (trabecular thickness) were measured with the Quantum FX microCT Imaging System.

Figure 12A:
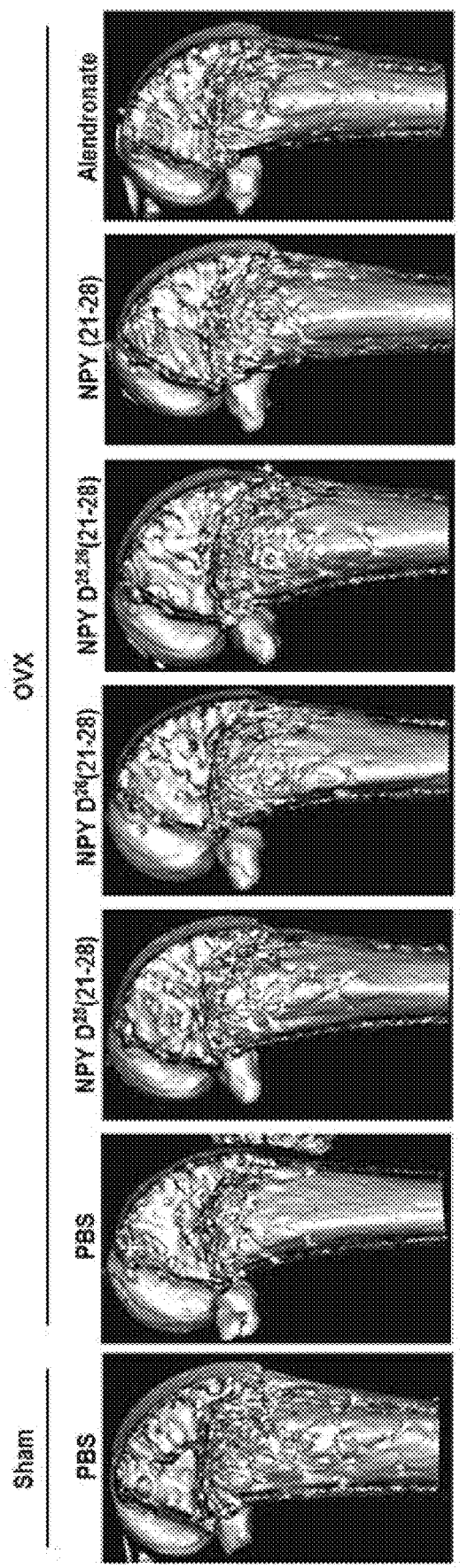
FIGS. 12A to 12C show the results of micro-CT imaging the overall bone density after administration of each peptide to animal models of osteoporosis (12A), and then graphically quantifying the change of bone density (12B) and the change of bone tissue thickness (12C) (Sham: control animal model with subcutaneous incision only, OVX: osteoporosis animal models with ovarian resection after subcutaneous incision).
Figure 12B:
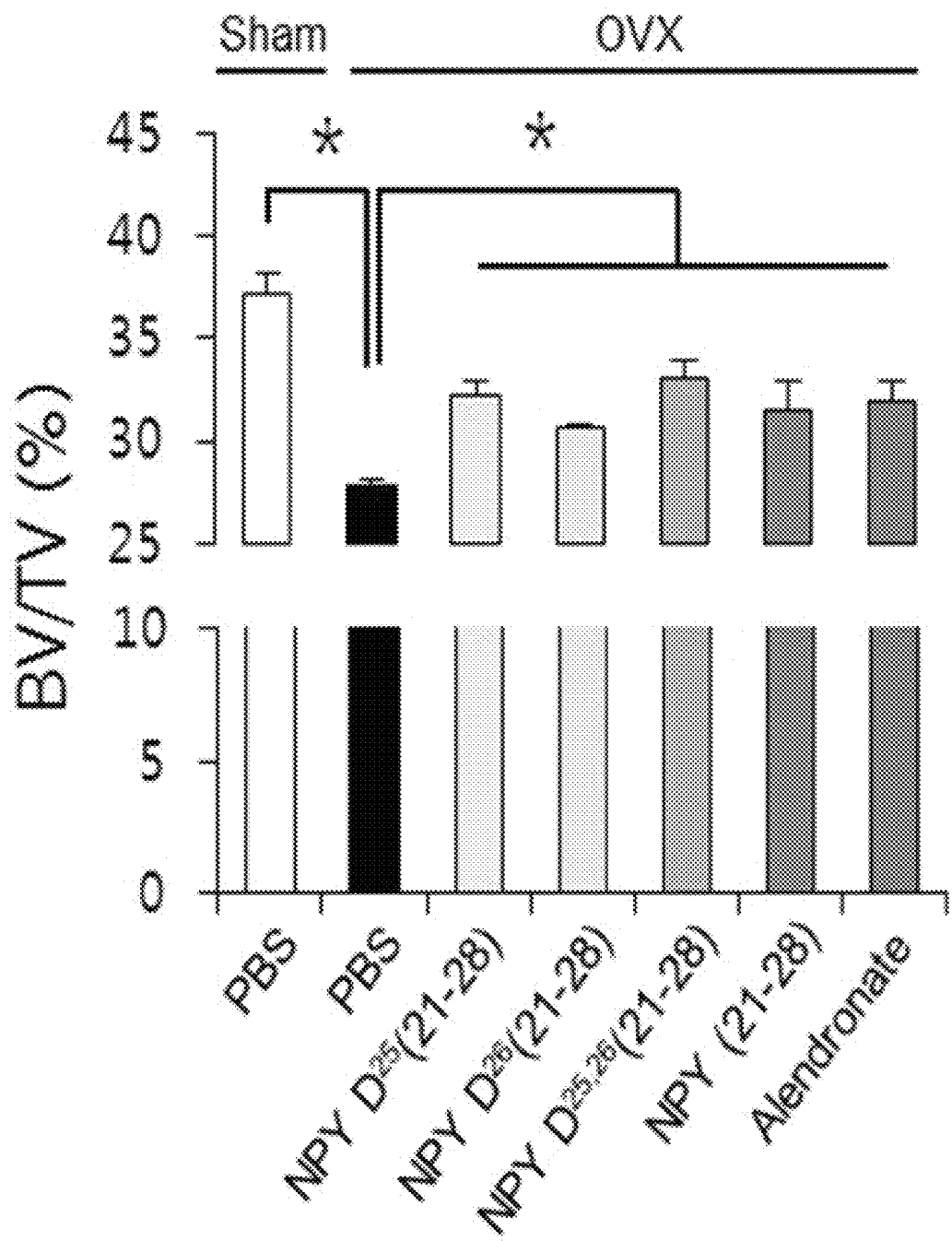
Figure 12C:
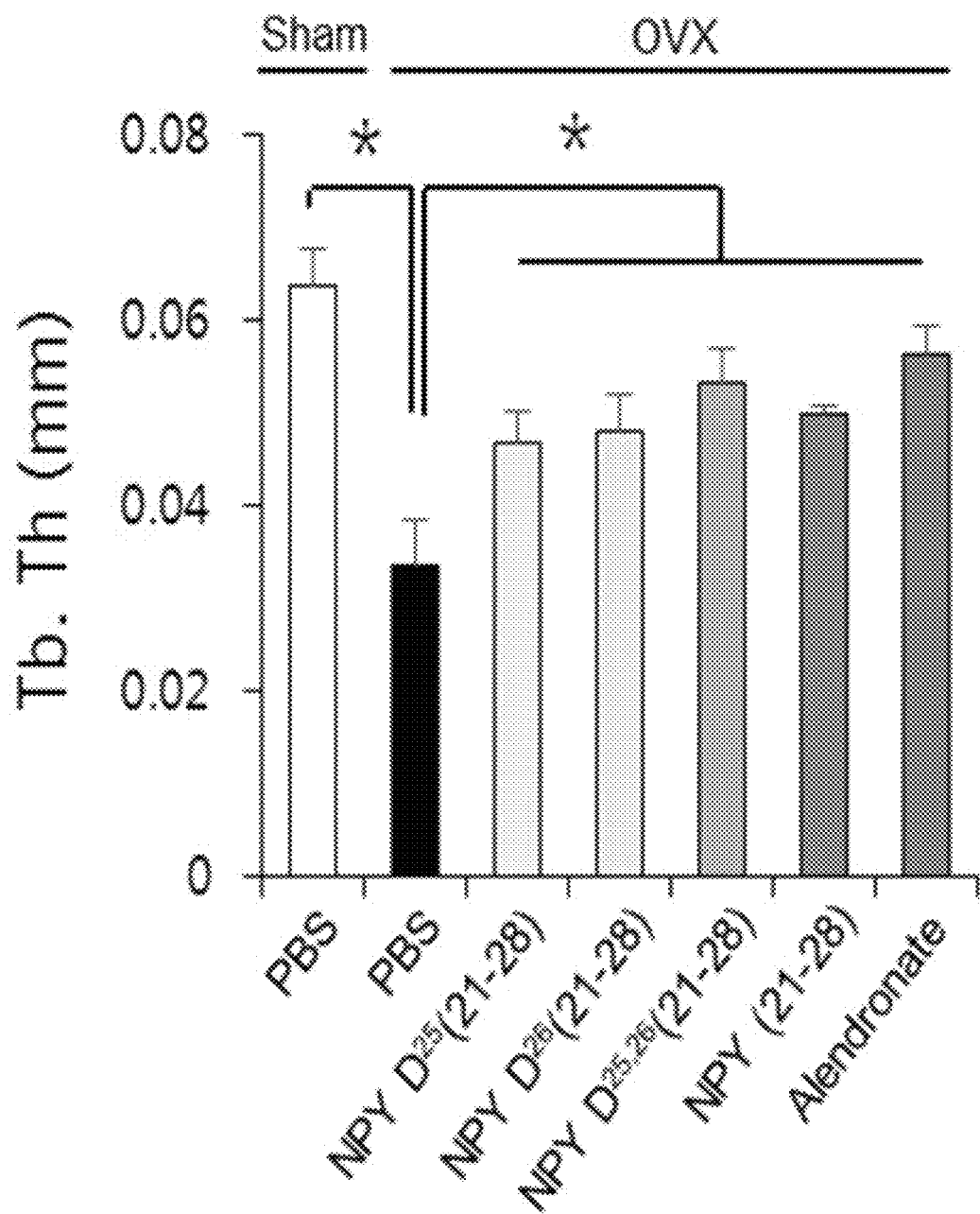

The results are shown in FIGS. 12A to 12C. As shown in FIGS. 12A to 12C, the microCT photographs showed that the percentage of bone density (BV/TV, %) and bone tissue thickness (trabecular thickness, mm) of the mice injected with NPY $D^{25}$(21-28), NPY $D^{26}$(21-28), and NPY $D^{25,26}$(21-28) in the animal models of osteoporosis were increased compared to the mice injected with PBS. In addition, this effect was equal to or higher than that of NPY (21-28), and the effect was similar to that of mice injected with the competitive drug Alendronate. In particular, animals treated with NPY $D^{25,26}$(21-28) showed the best effect (p<0.05, n=4-5 per group).

7-2. Osteoclast Changes in Bone Marrow by Administration of NPY $D^{25}$(21-28), NPY $D^{26}$(21-28), and NPY $D^{25,26}$(21-28) in Animal Models of Osteoporosis After the last administration at 4 weeks of NPY $D^{25}$(21-28), NPY $D^{26}$(21-28), and NPY $D^{25,26}$(21-28), the femurs were separated from the mice and the number of osteoclasts in the bone marrow was measured by TRAP staining.

Figure 13A:
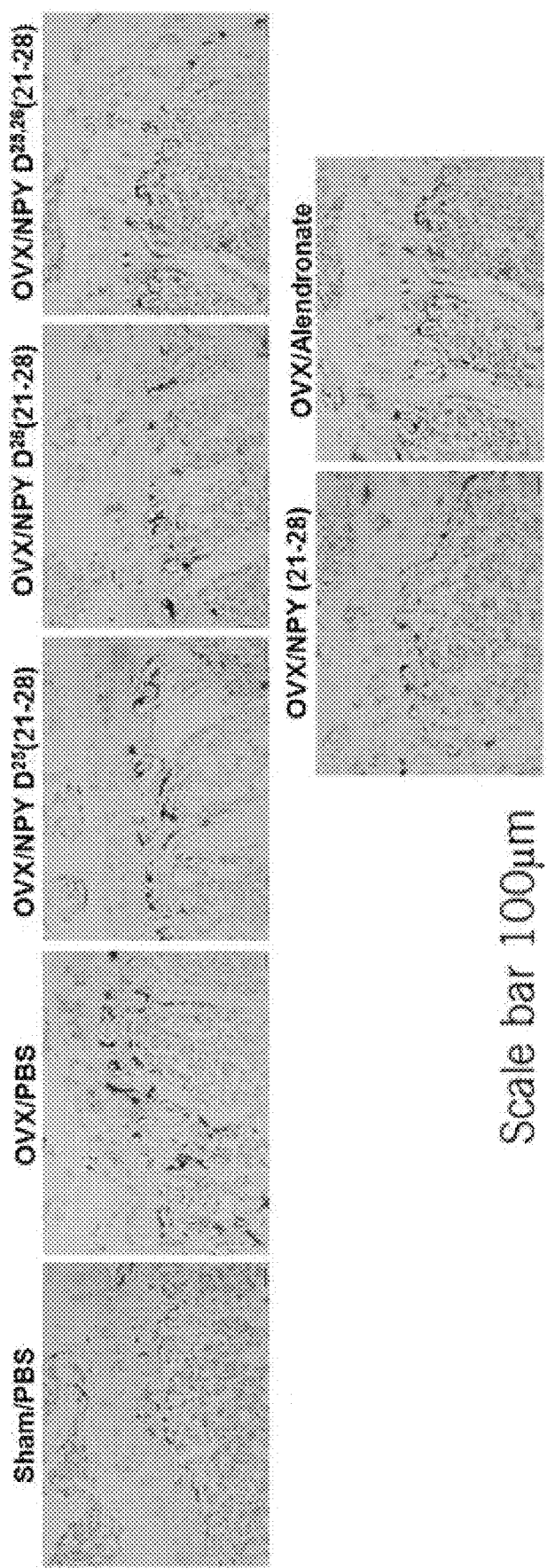
FIGS. 13A to 13C show the results of TRAP staining the change in the number of osteoclasts in bone marrow after administration of each peptide to animal models of osteoporosis (13A), and then graphically quantifying the number of osteoclasts (13B) and the surface area occupied by osteoclasts (13C) (Sham: control animal model with subcutaneous incision only, OVX: osteoporosis animal models with ovarian resection after subcutaneous incision).
Figure 13B:
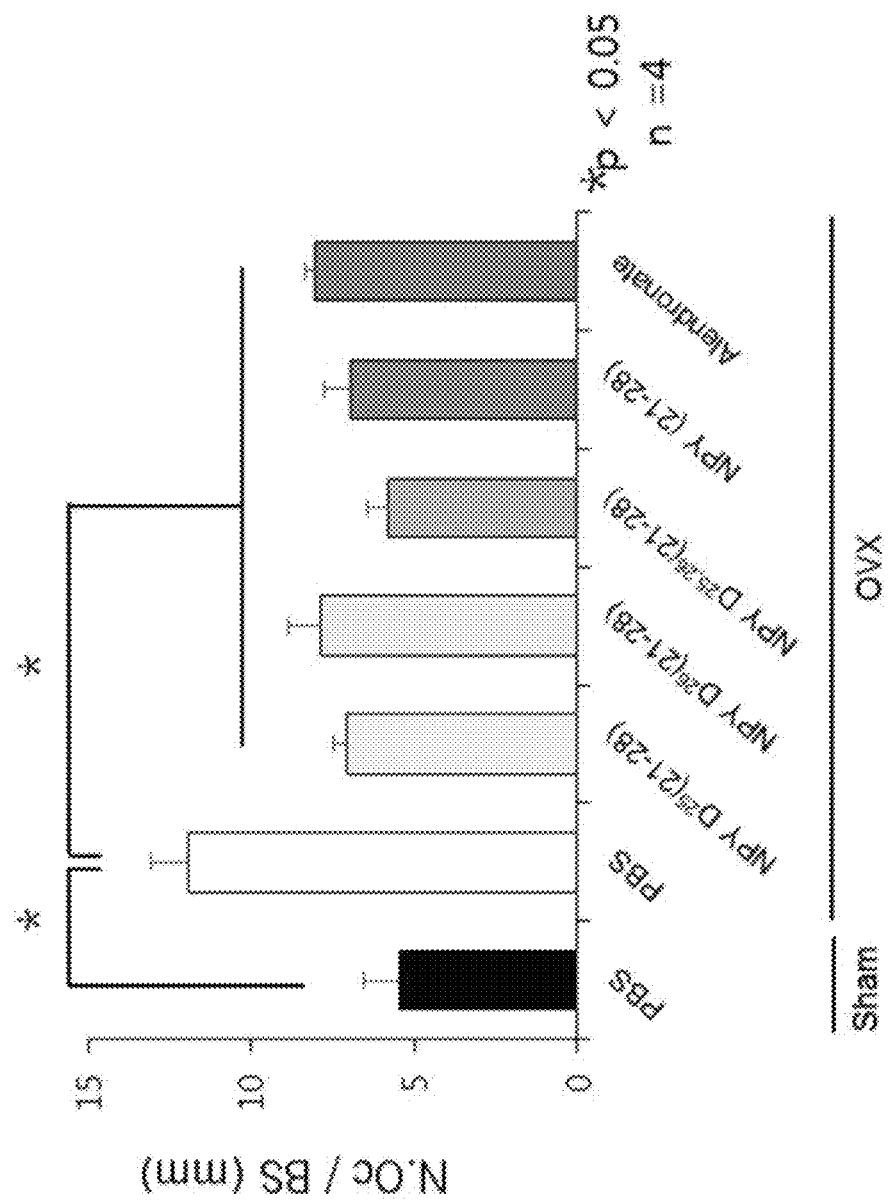
Figure 13C:
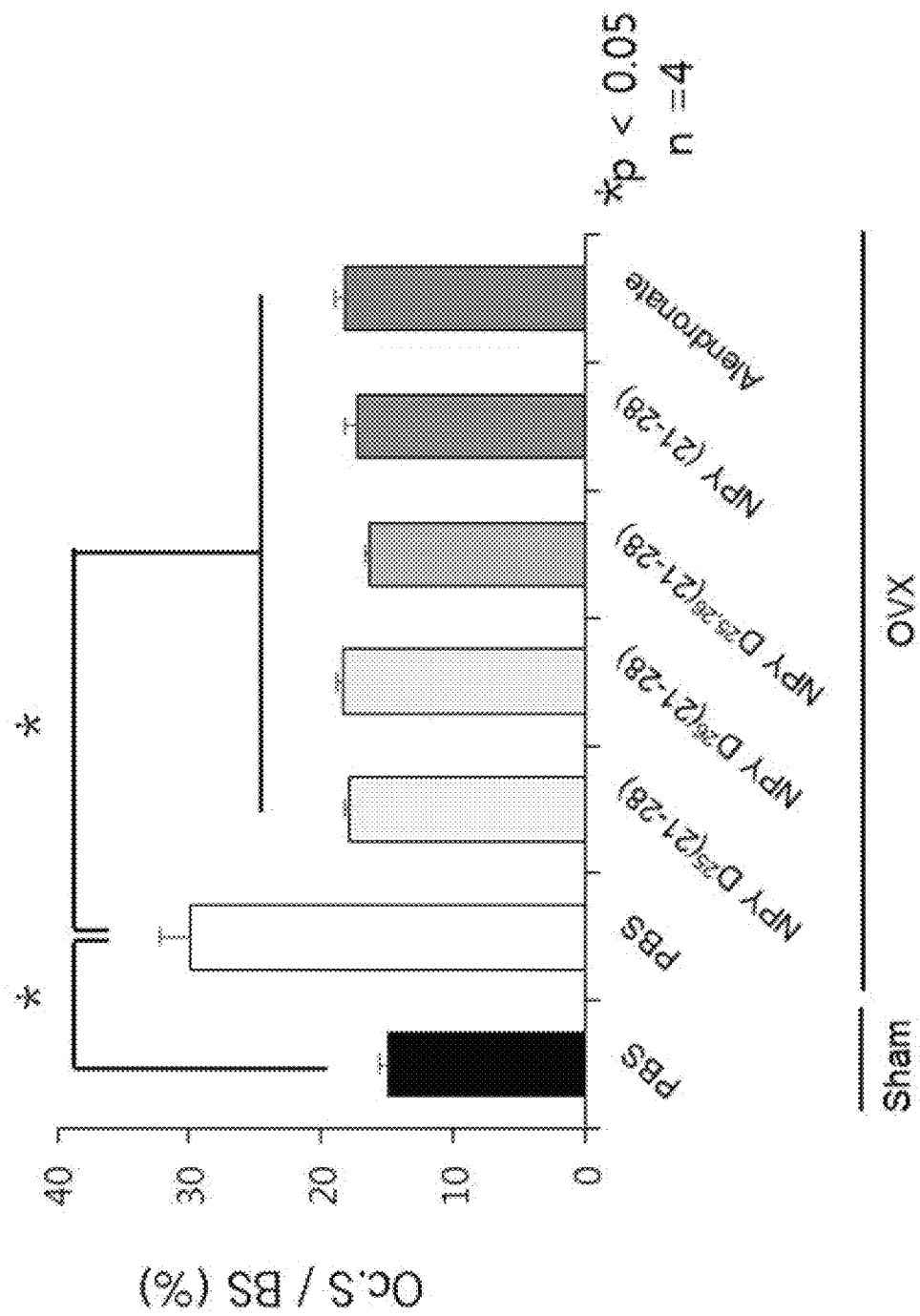

The results are shown in FIGS. 13A to 13C. As shown in FIGS. 13A to 13C, the number of TRAP positive osteoclasts in bone marrow of mice injected with NPY $D^{25}$(21-28), NPY $D^{26}$(21-28), and NPY $D^{25,26}$(21-28) (Number of osteoclast/Bone surface, mm) and the osteoclast surface (Osteoclast surface/Bone surface, %) were reduced compared to mice injected with PBS (p<0.05, n=4 per group). As with bone density, NPY $D^{25,26}$(21-28) was found to reduce osteoclasts in bone marrow with the highest efficiency.

7-3. Changes of Osteoblast in Bone Marrow by Administration of NPY $D^{25}$(21-28), NPY $D^{26}$(21-28), and NPY $D^{25,26}$(21-28) in Animal Models of Osteoporosis After the last administration of 4 weeks of NPY $D^{25}$(21-28), NPY $D^{26}$(21-28), and NPY $D^{25,26}$(21-28), the femurs were separated from the mice and the number of osteoblasts in bone marrow was measured by H & E staining.

Figure 14A:
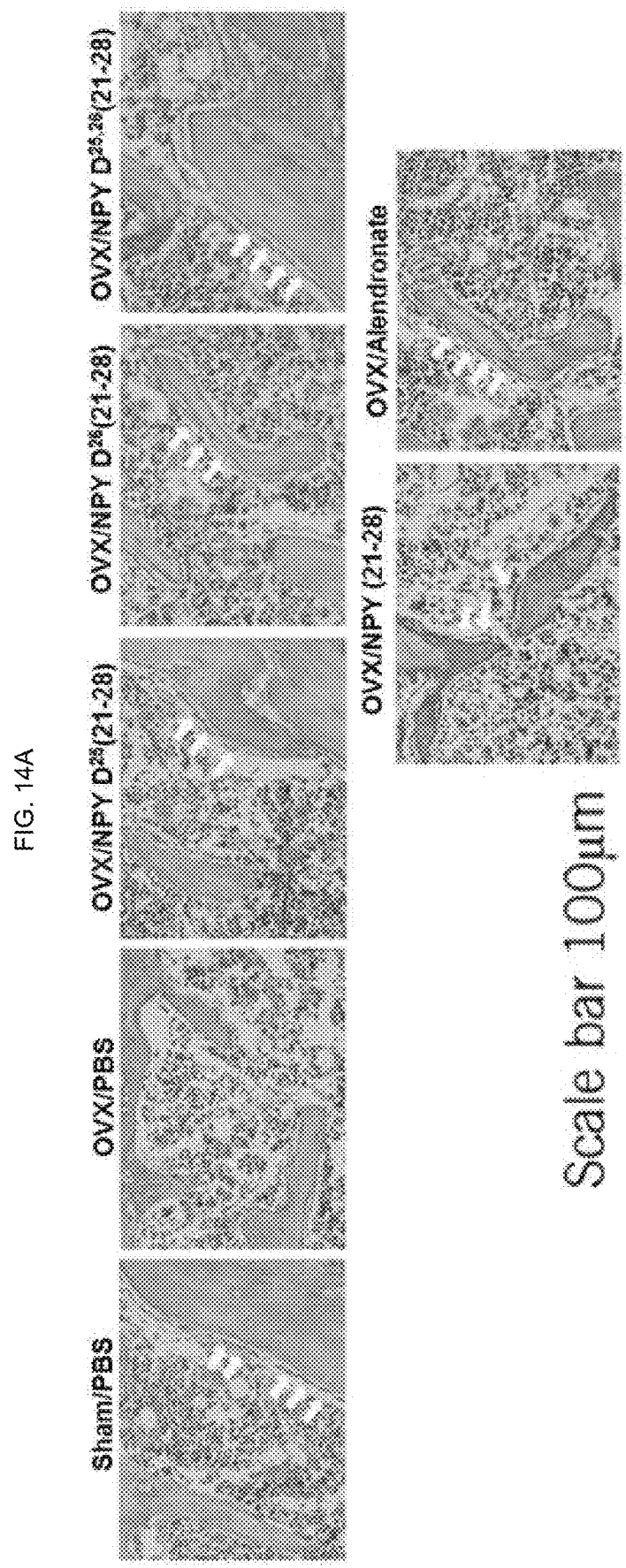
Figure 14B:
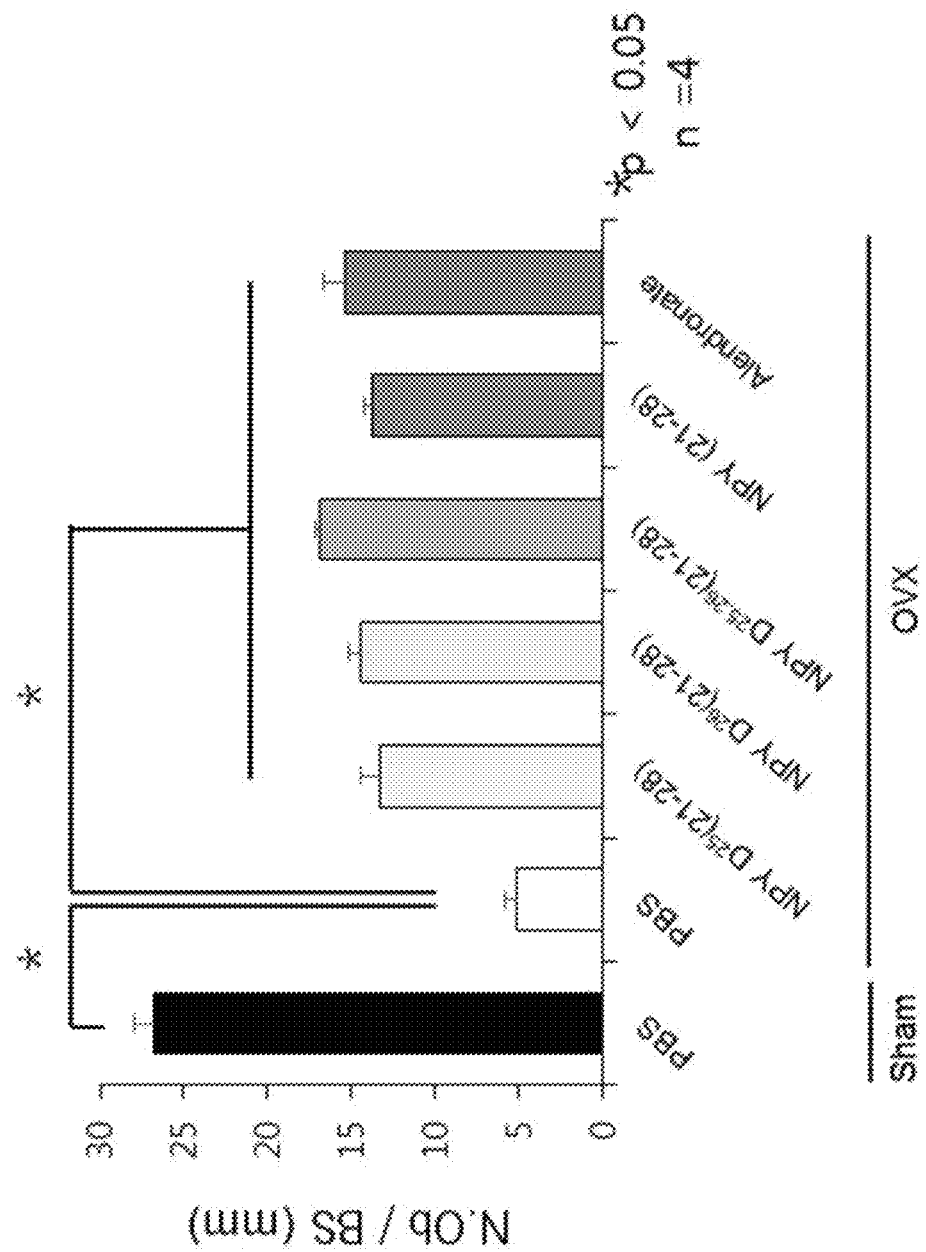

The results are shown in FIGS. 14A to 14C. As shown in FIGS. 14A to 14C, the number of osteoblast (Number of osteoblast/Bone surface, mm) and the osteoblast surface (Osteoblast surface/Bone surface, %) adjacent to the bone in the bone marrow of the mice to which NPY $D^{25}$(21-28), NPY $D^{26}$(21-28), and NPY $D^{25,26}$(21-28) were administered were increased compared to mice injected with PBS ($p<0.05$, n=4 per group).

From these results, it was found that NPY $D^{25}$(21-28), NPY $D^{26}$(21-28), and NPY $D^{25,26}$(21-28), which modified the structure of specific amino acids of NPY (21-28), inhibit the reduction in bone density and bone tissue thickness of osteoporosis mice by reducing the number of osteoclasts that differentiate from hematopoietic stem cells in the bone marrow and by simultaneously increasing the number of osteoblasts after inducing the release of myelopoiesis stem cells into blood in animal models of osteoporosis.

Therefore, it can be shown that NPY(21-28) and NPY $D^{25}$(21-28), NPY $D^{26}$(21-28), and NPY $D^{25,26}$(21-28) recombined through structural modifications therefrom are effective for preventing and treating osteoporosis. These short fragment peptides may not only have a better effect compared to the previously reported long peptides, but may also represent additional advantages such as improved stability, high absorption of tissue, and ease of manufacture.

INDUSTRIAL APPLICABILITY

The peptide consisting of the amino acid sequence of SEQ ID NO: 1 of the present invention effectively induces releasing hematopoietic stem cells into blood by reducing the expression level of hematopoietic stem cell adhesion factors in bone marrow. This induces a decrease in the number of osteoclasts in bone marrow and an increase in the number of osteoblasts, and has the effect of alleviating the decrease in bone density. Therefore, the peptide consisting of the amino acid sequence of SEQ ID NO: 1 of the present invention can be very usefully used for the development of a prophylactic or therapeutic agent for osteoporosis, which is highly likely to be used industrially.

---

What is claimed is:

1. A peptide consisting of the amino acid sequence of SEQ ID NO: 1, wherein at least one amino acid selected from the group consisting of the fifth and sixth amino acids of the amino acid sequence of SEQ ID NO: 1 is D-type.

2. The peptide according to claim 1, wherein the fifth and sixth amino acids of the amino acid sequence of SEQ ID NO: 1 are D-type.

3. A polynucleotide encoding the peptide of claim 1.

4. A composition comprising the peptide of claim 1 as an active ingredient.

5. The composition of claim 4, wherein the composition is a pharmaceutical composition or a food composition.

6. A method for treating any one disease selected from the group consisting of neutropenia, anemia and osteoporosis in a subject, the method comprising administering an effective amount of a composition to a subject in need thereof, wherein the composition comprises the peptide of claim 1 as an active ingredient.

7. The method of claim 6, wherein the neutropenia may be due to any one or more causes selected from the group consisting of radiation, alcoholism, drugs, allergic diseases, aplastic anemia, autoimmune diseases, T-γ lymphocyte proliferative diseases (T-γ LPD), myelodysplasia, myeloid fibrosis, dysgammaglobulinemia, paroxysmal nocturnal hemoglobinuria, cancer, vitamin B12 deficiency, folate deficiency, viral infection, bacterial infection, spleen disease, hemodialysis, or transplantation, leukemia, myeloma, lymphoma, metastatic solid tumors that infiltrate and replace the bone marrow, toxins, bone marrow failure, Schwarzmann-Diamond syndrome, cartilage-hair dysfunction, congenital dyskeratosis and type IB glycogen storage disease.

* * * * *